（12）United States Patent
Hirai et al.

(10) Patent No.: US 8,460,930 B2
(45) Date of Patent: Jun. 11, 2013

(54) METHOD FOR CONTROLLING PROLIFERATION OF CORD BLOOD HEMATOPOIETIC STEM CELLS AND USE THEREOF

(75) Inventors: Satoshi Hirai, Hiroshima (JP); Kasumi Ogata, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 13/146,613

(22) PCT Filed: Jan. 22, 2010

(86) PCT No.: PCT/JP2010/050795
§ 371 (c)(1),
(2), (4) Date: Jul. 27, 2011

(87) PCT Pub. No.: WO2010/087283
PCT Pub. Date: Aug. 5, 2010

(65) Prior Publication Data
US 2011/0287540 A1    Nov. 24, 2011

(30) Foreign Application Priority Data

Jan. 27, 2009 (JP) .................................. 2009-015639
Jan. 14, 2010 (JP) .................................. 2010-006277

(51) Int. Cl.
*C12N 5/00* (2006.01)
*C12M 1/00* (2006.01)

(52) U.S. Cl.
USPC ....................................................... 435/377

(58) Field of Classification Search
USPC ....................................................... 435/377
See application file for complete search history.

(56) References Cited

U.S. PATENT DOCUMENTS

| 6,733,433 B1 | 5/2004 | Fell |
| 2006/0251622 A1 | 11/2006 | Sazuki et al. |

FOREIGN PATENT DOCUMENTS

| EP | 2133086 | 12/2009 |
| JP | 11-127859 A | 5/1999 |
| JP | 2002-533171 | 10/2002 |
| JP | 2006-061106 A | 3/2006 |
| JP | 3788479 B2 | 4/2006 |
| JP | 2007-202506 A | 8/2007 |
| WO | WO 00/38762 | 7/2000 |
| WO | 2004/103440 | 12/2004 |
| WO | 2005/007799 | 1/2005 |
| WO | WO 2008/108412 | 9/2008 |

OTHER PUBLICATIONS

Yoon et al. (2009) Introducing pulsed low-intensity ultrasound to culturing human umbilical cord-derived mesenchymal stem cells, Biotechnology Letters, 31: 329-335.*
Broxmeyer et al. (1990) Human umbilical cord blood: A clinically useful source of transplantable hematopoietic stem/progenitor cells, International Journal of Cell Cloning, 8:76-91 Suppl. 1.*
Kurata, et al., "Effect of cord blood serum on expansion of BM cells in liquid culture", The Jpn. J. Obstet. Gynecol. Neonatal Hematol., 1993, vol. 3, No. 2, p. S141-S142.
Konishi, "Ex vivo Expansion of Cord Blood Hemopoietic Stem Cells by Stem Cell Factor (SCF) Interleukin-3 Intererleukin-6 and Cord Plasma: A Fundamental Strudy for Cord Blood Stem Cell Transplantation", Kanazawa University J. Juzen Med. Soc., 1994, vol. 103, No. 2., p. 381-393 (with Abstract p. 393).
Wada et al, "Sensitivity test for anti-tumor agents. I. Application of human cord serum—as cellular growth factor", Jpn J Cancer Chemother, 1990, vol. 17, No. 1, p. 97-102 (with Abstract p. 101).
Knudtzon, et al., "The Effect of Sonicated Serum on Growth of Normal and Leukaemic Human Cells in Agar Cultures", Scandinavian Journal of Haematology, 1979, vol. 22, pp. 296-304.
Verfallie, "Soluble Factor(s) Produced by Human Bone Marrow Stroma Increase Cytokine-Induced Proliferation and Maturation of Primitive Hematopoietic Progenitors while Preventing their Terminal Differentiation", Blood, 1993, vol. 82, No. 7, pp. 2045-2053.

* cited by examiner

*Primary Examiner* — Karen Cochrane Carlson
*Assistant Examiner* — Jennifer M. H. Tichy
(74) *Attorney, Agent, or Firm* — Hamre, Schumann, Mueller & Larson, P.C.

(57) ABSTRACT

The present invention provides a method for controlling the proliferation and differentiation of cord blood-derived hematopoietic stem cells with excellent safety when proliferating them by culturing. The hematopoietic stem cells are inoculated into a medium containing a sonicated liquid component of cord blood. The proliferation and differentiation of the cord blood hematopoietic stem cells can be inhibited in the presence of the sonicated liquid component of cord blood. On the contrary, the proliferation of cord blood hematopoietic stem cells can be accelerated by inoculating the hematopoietic stem cells into a medium containing a non-sonicated liquid component of cord blood. Thus, according to the present invention, by using serum derived from cord blood, it is possible to regulate the inhibition of the proliferation and differentiation of cord blood hematopoietic stem cells and the acceleration of the proliferation of the same as desired.

9 Claims, 6 Drawing Sheets

METHOD FOR CONTROLLING PROLIFERATION OF CORD BLOOD HEMATOPOIETIC STEM CELLS AND USE THEREOF

This application claims the benefit of priority of Japanese applications: JP2009-015639, filed Jan. 27, 2009; and JP2010-006277, filed Jan. 14, 2010; and PCT/JP2010/050795, filed Jan. 22, 2010, entitled "Method for Controlling Propagation of Umbilical Cord Blood Hematopoietic Stem Cells and Use Thereof."

TECHNICAL FIELD

The present invention relates to a method for controlling the proliferation of cord blood-derived hematopoietic stem cells and the use thereof. More specifically, the present invention further relates to a method for producing the hematopoietic stem cells, and to a proliferation-controlling agent, a proliferation-controlling kit, and a cord blood component preparation device used in the control method.

BACKGROUND ART

Hematopoietic stem cells are multipotent stem cells having self-renewal potential and capable of differentiating into all types of hematopoietic cells such as leukocytes, erythrocytes, and platelets. They are present in bone marrow fluid, peripheral blood, and cord blood. It is known that hematopoietic stem cell transplant, which is the transplant of hematopoietic stem cells into a body, is an effective way of treating intractable blood disease such as leukemia. Although hematopoietic stem cells in bone marrow fluid or peripheral blood generally are used for the treatment, there is a problem in that their collection places a considerable burden on donors. In contrast, cord blood is obtained secondarily at the time of delivery, so that it places a lower burden on donors. Besides, cord blood is excellent in transplant compatibility. Thus, cord blood is attracting attention as a supply source of hematopoietic stem cells.

However, the amount of cord blood obtained from a donor is smaller than the amount of bone marrow fluid or peripheral blood, so that the cord blood may fail to provide a sufficient number of cells necessary for transplant. As a remedy therefor, there has been developed a method for proliferating cord blood-derived hematopoietic stem cells by culturing so that they can be used for transplant. As a specific example thereof, a method for accelerating the proliferation of the hematopoietic stem cells by culturing them together with mesenchymal stem cells, feeder cells derived from an animal of a different species, or the like has been reported (Patent Document 1 and Patent Document 2). When culturing the hematopoietic stem cells, it is desired to inhibit the proliferation and differentiation until a desired time, for example. Thus, for example, a method in which a virus vector incorporating a differentiation-inhibiting gene is transfected into the hematopoietic stem cells has been reported (Patent Document 3). However, regarding the method including the transfection of the virus vector, there is a fear that it may affect the expression of other genes, so that its safety might be insufficient, for example. It also has a problem of cumbersome operations and high cost.

CITATION LIST

Patent Document

[Patent Document 1] JP 2006-61106 A
[Patent Document 2] JP 2007-202506 A
[Patent Document 3] JP 1999-127859 A

BRIEF SUMMARY OF THE INVENTION

Problem to be Solved by the Invention

With the foregoing in mind, it is an object of the present invention to provide a method for controlling the proliferation and differentiation of cord blood-derived hematopoietic stem cells with excellent safety when proliferating them by culturing.

Means for Solving Problem

In order to achieve the above object, a control method according to the present invention is a method for controlling proliferation of cord blood hematopoietic stem cells, including the step of:
(X) inhibiting proliferation and differentiation of hematopoietic stem cells by culturing the hematopoietic stem cells in a medium containing a sonicated liquid component of cord blood.

A production method according to the present invention is a method for producing cord blood hematopoietic stem cells, including the step of controlling proliferation of hematopoietic stem cells by the control method according to the present invention.

A proliferation-controlling agent according to the present invention is a proliferation-controlling agent for use in the control method according to the present invention. The proliferation-controlling agent contains:
(a) a proliferation inhibitor for inhibiting proliferation and differentiation of the hematopoietic stem cells, the proliferation inhibitor containing a sonicated liquid component of cord blood.

A proliferation-controlling kit according to the present invention is a proliferation-controlling kit for use in the control method according to the present invention. The proliferation-controlling kit includes the proliferation inhibitor (a).

Effects of the Invention

According to the present invention, it is possible to control the proliferation and differentiation of cord blood hematopoietic stem cells using the liquid component derived from cord blood without using a virus vector having a problem in safety as described above, for example. Specifically, it is possible to inhibit the proliferation and differentiation using only a sonicated liquid component of cord blood. Therefore, the present invention is very excellent in safety and can regulate the proliferation and differentiation with simple operations. In particular, since the present invention uses a liquid component of cord blood, it is possible to use a liquid component derived from cord blood of the same individual as the hematopoietic stem cells, for example. Therefore, cord blood can be used more effectively, and since the components derived from the same individual can be used in combination, the reliability regarding the safety also can be improved. As described above, since the present invention can inhibit the proliferation and differentiation of cord blood hematopoietic stem cells, it is particularly useful when delivering the hematopoietic stem cells to a destination, storing the hematopoietic stem cells until a desired time at which the proliferation of the hematopoietic stem cells is started, and the like, for example. Thus, it can be said that the method according to the present invention can promote further the effective utilization of cord blood hematopoietic stem cells in the field of regenerative medicine.

MODE FOR CARRYING OUT THE INVENTION

<Proliferation Control Method>

Figure 1:
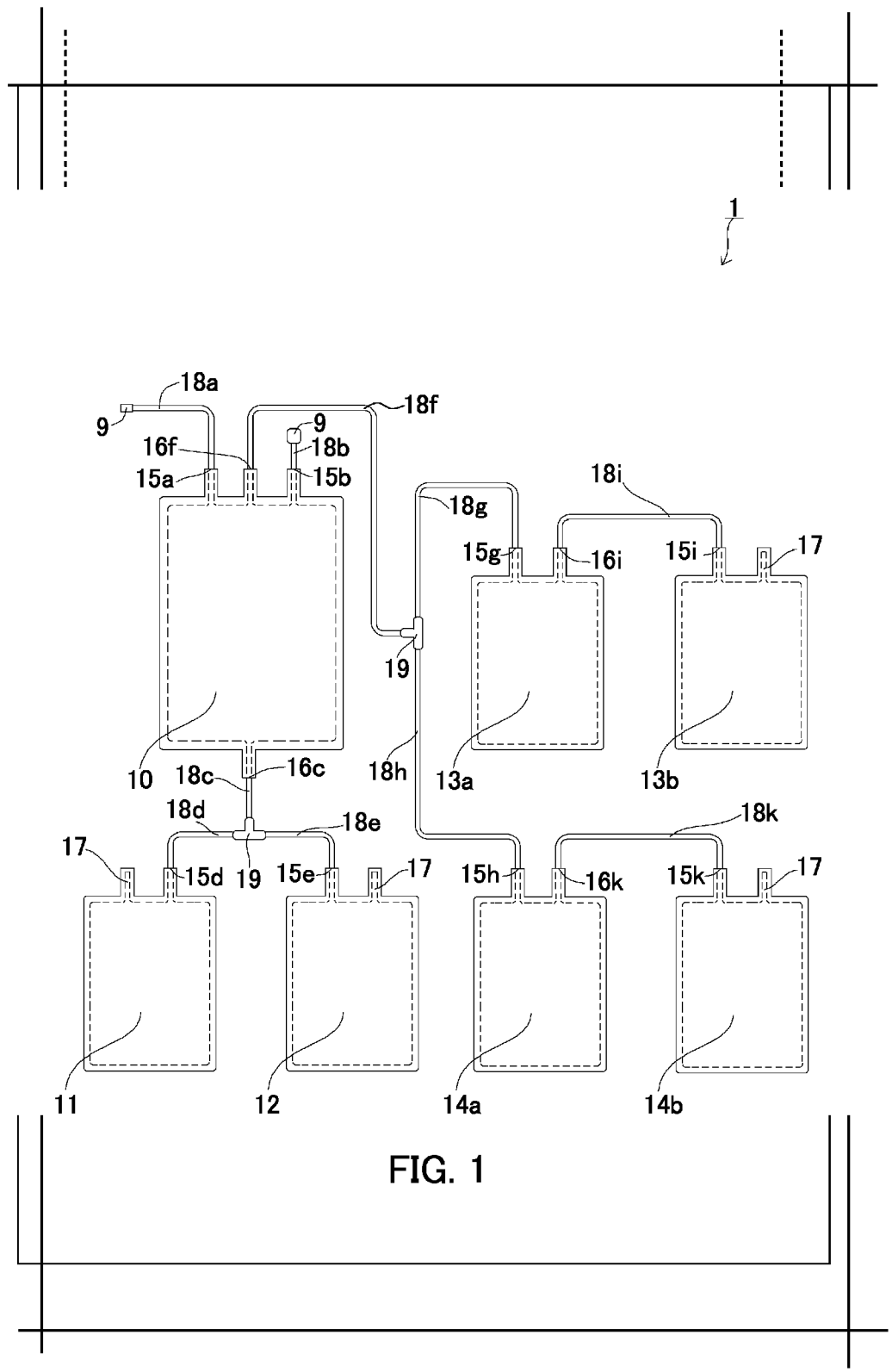
FIG. 1 is a plan view schematically showing an example of a cord blood component preparation device according to the present invention.

The control method according to the present invention is, as described above, a method for controlling proliferation of cord blood hematopoietic stem cells, including the step of:
(X) inhibiting proliferation and differentiation of hematopoietic stem cells by culturing the hematopoietic stem cells in a medium containing a sonicated liquid component of cord blood.

In the present invention, the sonicated liquid component of cord blood hereinafter also is referred to as the "treated liquid component". In general, blood is roughly composed of a liquid component (liquid fraction) and a cell component (cell fraction). The liquid component is serum or plasma, for example. The cell component is a blood cell component (blood cell fraction), which includes erythrocytes, leukocytes, and platelets, for example. In the present invention, the liquid component may be either serum or plasma, for example. In the present invention, it is only necessary that the medium contains the liquid component, and other configurations are by no means limited. Although the liquid component of cord blood contained in the medium further may contain, for example, cord blood-derived components such as the cell component and a blood coagulation factor, it is preferable that the liquid component of cord blood contained in the medium is: a liquid component obtained by removing the cell component from the cord blood; a liquid component obtained by removing the blood coagulation factor from the cord blood; or a liquid component obtained by removing the cell component and the blood coagulation factor from the cord blood. It is to be noted that the removal of the cell component and the removal of the blood coagulation factor are not limited to complete removal thereof from the cord blood. The blood coagulation factor is fibrinogen (Factor I), prothrombin (Factor II), or the like, for example.

In the present invention, the cord blood to be sonicated is not particularly limited, and may be, for example, the cord blood itself or a liquid component thereof. A liquid component before sonication hereinafter also is referred to as a "not-yet-treated liquid component". Examples of the liquid component include plasma and serum. The "plasma" generally is a liquid fraction obtained by removing the blood cells from blood, and the "serum" generally is a liquid fraction obtained by removing the blood cells and some kinds of blood coagulation factors from blood. In the case where the liquid component is sonicated, the liquid component may be, for example, any of: a liquid fraction obtained by removing the blood cell component from cord blood; a liquid fraction obtained by removing the blood coagulation factor from cord blood; and a liquid fraction obtained by removing the blood cell component and the blood coagulation factor from cord blood. Among them, a liquid fraction obtained by removing the blood cell component from cord blood is preferable, for example. Furthermore, in the case where the liquid component is sonicated, the liquid component may contain platelets, for example. Examples of plasma containing the platelets include so-called platelet-rich plasma.

In the present invention, the treated liquid component may be prepared by sonicating cord blood itself and then collecting a liquid component, or by collecting a liquid component from cord blood and then sonicating the thus-collected liquid component, for example. When collecting the liquid component from the cord blood, it is preferable to remove not only the blood cells but also blood coagulation factors such as fibrinogen, for example.

In the present invention, the liquid component (treated liquid component) of cord blood preferably is serum (treated serum) obtained from sonicated cord blood plasma, for example.

The present invention further may include the step of:
(Y) accelerating proliferation of the hematopoietic stem cells by culturing the hematopoietic stem cells in a medium containing a non-sonicated liquid component of cord blood.

The non-sonicated liquid component of cord blood hereinafter is referred to as the "untreated liquid component". Similarly to the above-described treated liquid component, examples of the untreated liquid component also include plasma and serum.

In the present invention, either the step (X) of inhibiting the proliferation and differentiation or the step (Y) of accelerating the proliferation may be performed first, for example. The method according to a first embodiment is such that, for example, first, in the step (X), proliferation and differentiation of the hematopoietic stem cells are inhibited using the treated liquid component, and thereafter, in the step (Y), the proliferation of the hematopoietic stem cells inhibited in the step (X) is accelerated using the untreated liquid component. According to this embodiment, it is possible to inhibit the proliferation and differentiation of the hematopoietic stem cells until a desired time so as to start the proliferation of the hematopoietic stem cells at the desired time. That is, it is possible to control the ON-OFF of the proliferation of the hematopoietic stem cells easily merely by changing the serum to be used.

Furthermore, the method according to a second embodiment is such that, for example, first, in the step (Y), the proliferation of the hematopoietic stem cells is accelerated using the untreated liquid component, and thereafter, in the step (X), proliferation and differentiation of the hematopoietic stem cells proliferated in the step (Y) are inhibited using the treated liquid component. According to this embodiment, the proliferated hematopoietic stem cells can be stored while preventing further proliferation and differentiation thereof until a desired time.

In the present invention, hematopoietic stem cells to be controlled are derived from cord blood, and serum used to control the proliferation of the hematopoietic stem cells also is derived from cord blood. Thus, in the present invention, it is possible to use cord blood hematopoietic stem cells and a liquid component of cord blood derived from the same individual, for example. Specifically, the proliferation and differentiation can be inhibited using hematopoietic stem cells and a treated liquid component derived from cord blood of the same individual, and further, the proliferation can be accelerated using an untreated liquid component derived from the cord blood of the same individual. Thus, among components of cord blood, not only hematopoietic stem cells but also a liquid component can be used to control the proliferation of the hematopoietic stem cells, so that the cord blood can be utilized still more effectively.

The individual is not particularly limited, and examples thereof include: humans; rodents; domestic animals; and mammals such as primates, excluding humans.

In the present invention, the method for preparing hematopoietic stem cells is not particularly limited, and any conventionally known method can be employed. An example of the method will be described below, but the method is not limited thereto. First, erythrocytes in cord blood are caused to sediment, and a supernatant fraction is collected. Cord blood is blood contained in a placenta and an umbilical cord. It generally is collected from a placenta and an umbilical cord during or after a delivery and placed in a blood collection bag containing an anticoagulant at a hospital. An erythrocyte sedimenting agent for separating erythrocytes is added to the cord blood containing the anticoagulant. Examples of the erythrocyte sedimenting agent include HES (Hydroxy Ethyl Starch). The amount of the erythrocyte sedimenting agent to be added is not particularly limited. Preferably, the erythrocyte sedimenting agent is added to cord blood so that its concentration becomes 1 to 50 mg/ml, for example. By allowing the cord blood containing the erythrocyte sedimenting agent to stand still, the cord blood separates into a fraction containing erythrocytes and a supernatant fraction containing hematopoietic stem cells. The conditions for carrying out this separation are not particularly limited. For example, the separation is carried out at a temperature from 15° C. to 25° C. For example, when the cord blood contains the erythrocyte sedimenting agent in advance, it is not necessary to add the erythrocyte sedimenting agent (the same applies hereinafter).

Next, the supernatant fraction is separated into a sediment fraction containing hematopoietic stem cells and a liquid fraction (supernatant fraction) by centrifuging. The conditions for the centrifuging are not particularly limited, and are as follows, for example: the centrifugal acceleration is 10780 to 43120 m/s$^2$ (1100 to 4400×g); the temperature is 2° C. to 37° C.; and the time is 4 to 30 minutes. In the present invention, it is preferable to use hematopoietic stem cells and a liquid fraction derived from the same individual, as described above. Thus, the liquid fraction obtained after centrifuging preferably is used for the preparation of the liquid component, as will be described below. The liquid fraction obtained after the centrifuging may be a fraction containing plasma (plasma fraction) or a fraction containing serum (serum fraction), for example. Furthermore, the liquid fraction obtained after centrifuging further may contain, for example, platelets, as described above. As described above, the liquid component may be prepared from a liquid component containing platelets, for example. Thus, when collecting the sediment fraction, centrifuging may be carried out under conditions such that the liquid fraction obtained after centrifuging contains platelets, for example. Such conditions are not particularly limited, and centrifuging can be carried out according to a conventionally known method for collecting platelet-rich plasma, for example. Specifically, the conditions are as follows, for example: the centrifugal acceleration is 2940 to 11760 m/s$^2$ (300 to 1200×g), the temperature is 1° C. to 20° C., and the time is 3 to 6 minutes.

Subsequently, hematopoietic stem cells are purified from the sediment fraction. Specifically, first, magnetic beads having an anti-CD34 antibody immobilized thereon are added to the sediment fraction, thereby causing CD34 of the hematopoietic stem cells to react with the anti-CD34 antibody on the magnetic beads. Through this antigen-antibody reaction, the hematopoietic stem cells are bound to the magnetic beads. Subsequently, the sediment fraction to which the magnetic beads have been added is applied to a magnetic column so as to trap the magnetic beads in the column by a magnetic force, and unnecessary components in the sediment fraction are removed. In this manner, purified hematopoietic stem cells can be prepared.

In the present invention, the method for preparing a treated liquid component derived from cord blood is not particularly limited. In the present invention, it is preferable to use hematopoietic stem cells and a liquid component derived from cord blood of the same individual. Thus, as an illustrative example, a method for carrying out the preparation of the liquid component along with the above-described preparation of hematopoietic stem cells will be described.

First, in the manner described above, cord blood is separated into a sediment fraction containing hematopoietic stem cells and a liquid fraction (supernatant fraction). The liquid fraction may be, for example, a plasma fraction or a serum fraction, as described above. Then, the liquid fraction is sonicated. The method for carrying out the sonication is not particularly limited, and examples thereof include the following method. The conditions for the sonication are not particularly limited. For example, the sonication is carried out under the conditions where, when ultrasonic waves against an object to be treated are measured with a sound pressure meter, a sound pressure of at least 5 mV can be obtained, with the frequency being set to, for example, 28 to 100 kHz, the distance from an ultrasonic generator being set to, for example, 5 to 30 cm, and the treatment time being set to, for example, 5 to 60 minutes, preferably 10 to 30 minutes. In the present invention, ultrasonic waves can be generated using an ordinary ultrasonic generator, for example. The treated liquid component can be obtained in this manner.

In the case where the liquid fraction contains a blood coagulation factor such as fibrinogen, for example, the blood coagulation factor further is removed from the liquid fraction, and the liquid fraction after the removal can be used as the treated liquid component, for example. Specifically, for example, when the liquid fraction is a plasma fraction containing the blood coagulation factor, it is preferable that the blood coagulation factor is removed, serum is collected, and the thus-collected serum is used as the treated liquid fraction. The removal of the blood coagulation factor may be performed either before or after the sonication, for example. The method for removing the blood coagulation factor is not particularly limited, and examples thereof include a method in which a blood coagulation factor such as fibrinogen is denatured and then removed as an insoluble fraction. A specific example thereof is a method in which fibrinogen is denatured so as to form fibrin and the thus-formed fibrin is removed as an insoluble fraction, for example. The denaturing method is not particularly limited, and examples thereof include thermal denaturation. Specifically, examples of the denaturing method include heat-treating the liquid fraction. The heating conditions are not particularly limited, and are as follows, for example: the heating temperature preferably is 50° C. to 60° C.; and the heating time preferably is 10 to 120 minutes, more preferably 30 to 60 minutes. The insoluble fraction can be removed by allowing the heat-treated liquid fraction to stand still, centrifuging the heat-treated liquid fraction, or filtering the heat-treated liquid fraction, for example. Then, the treated liquid component is obtained by collecting a supernatant fraction obtained after the standing still, the supernatant fraction obtained after the centrifuging, or a filtrate obtained after the filtration, for example. The conditions for the standing still, centrifuging, filtering, or the like are by no means limited, and conventionally known conditions can be employed. Furthermore, examples of the method for removing the blood coagulation factor from the liquid fraction include, in addition to the above methods, methods utilizing the activation mechanism of a blood coagulation system, e.g., adding a coagulation factor such as calcium chloride or thrombin to the liquid fraction. Specific conditions thereof are by no means limited, and conventionally known conditions can be employed.

On the other hand, the untreated liquid component can be prepared in the same manner as in the above, except that the sonication is not performed, for example.

In the present invention, the step (X), i.e., the step of inhibiting the proliferation and differentiation of hematopoietic stem cells, can be carried out by inoculating the hematopoietic stem cells into a medium containing the sonicated liquid component, as described above. As a specific example thereof, an example where the treated liquid component serum is treated serum will be described below. It is to be noted, however, that the present invention is not limited thereto, and treated liquid components other than serum also can be used, for example.

It is only necessary that the medium contains the treated serum, and other configurations and conditions are by no means limited. Examples of the medium include media that can be used for culturing hematopoietic stem cells of cord blood. As specific examples, an Iscove's modified Dulbecco's medium (IMDM), an X-VIVO medium, a STEM-LINE medium, and the like can be used. The concentration of the treated serum in the medium is not particularly limited, and is, for example, 0.01 to 20 v/v %, preferably 0.1 to 10 v/v %, and more preferably 2.5 to 10 v/v %. The number of hematopoietic stem cells per 1 ml of the medium is 1000 to 100000, for example. The medium further may contain additives, and examples of the additives include cytokine, antibiotics, salts, and vitamins.

The hematopoietic stem cells inoculated into the medium containing the treated serum may be placed under ordinary culture conditions for proliferating hematopoietic stem cells, for example. According to the present invention, since the medium contains the treated serum as described above, the proliferation and differentiation of the hematopoietic stem cells can be inhibited by culturing them in the medium. The temperature at the time of culturing is 37° C., for example. Furthermore, the hematopoietic stem cells may be placed in the same medium for about 1 to 7 days, for example, and the medium preferably is replaced with a new medium every 1 to 7 days. By such replacement of the medium, it is possible to inhibit the proliferation and differentiation of the hematopoietic stem cells for 1 to 7 days, for example, and further, by accelerating the proliferation as will be described below, it is also possible to start the proliferation. A method for replacing the medium with a new medium is by no means limited, and examples thereof include: replacing the medium at predetermined times, as described above; and supplying a new medium continuously or intermittently. When the latter is employed, it is preferable to discard a part of the old medium continuously or intermittently, for example.

In the present invention, the step (Y), i.e., the step of accelerating the proliferation of hematopoietic stem cells, can be carried out by inoculating the hematopoietic stem cells into a medium containing non-sonicated serum, as described above. A specific example thereof will be described below. It is to be noted, however, the present invention is by no means limited to this specific example.

As the medium, it is possible to use the same medium as described above except that it contains the untreated serum instead of the treated serum. The concentration of the untreated serum in the medium is not particularly limited, and is, for example, 0.01 to 20 v/v %, preferably 0.1 to 10 v/v %, and more preferably 2.5 to 10 v/v %. The number of hematopoietic stem cells per 1 ml of the medium is, for example, 1000 to 100000. The medium further may contain the same additive as described above. The additives are not particularly limited and may be the same as described above.

The hematopoietic stem cells inoculated into the medium containing the untreated serum may be subjected to ordinary culture conditions for proliferating hematopoietic stem cells, for example. The temperature at the time of culturing is 37° C., for example. Furthermore, the hematopoietic stem cells may be placed in the same medium for about 1 to 7 days, for example, and the medium preferably is replaced with a new medium every 1 to 7 days. By culturing the hematopoietic stem cells in the medium containing the untreated serum, the number of the cells inoculated initially can be increased about 2- to 10-fold through 7 days of culturing, for example.

In the present invention, for example, when the step (Y) is performed after the step (X) of inhibiting the proliferation and differentiation, i.e., when the proliferation and differentiation are inhibited until a desired time and the proliferation is started to be accelerated from a desired time, the medium containing the treated serum may be replaced with the medium containing the untreated serum. On the other hand, for example, when the step (Y) is performed prior to the step (X) of inhibiting the proliferation and differentiation, i.e., when hematopoietic stem cells are proliferated, and differentiation and further proliferation of the proliferated hematopoietic stem cells are inhibited until a desired time, the medium containing the untreated serum may be replaced with the medium containing the treated serum. When the step (X) and the step (Y) are repeated, the medium may be replaced depending on the purpose, as described above.

<Production Method>

The production method according to the present invention is, as described above, a method for producing cord blood hematopoietic stem cells, including the step of controlling proliferation of hematopoietic stem cells by the control method according to the present invention.

The production method according to the present invention is characterized in that the control method according to the present invention is used in the inhibition of proliferation and differentiation of hematopoietic stem cells, and other conditions and configurations are by no means limited. Unless otherwise stated, it can be carried out in the same manner as the control method according to the present invention.

The production method according to the present invention includes the step (X) as the step of inhibiting proliferation and differentiation of hematopoietic stem cells, and preferably further includes the step of accelerating proliferation of the hematopoietic stem cells. The acceleration step is, for example, the step of accelerating the proliferation of the hematopoietic stem cells by inoculating cord blood hematopoietic stem cells into a medium containing a liquid component of blood, and preferably is the step (Y) in the control method according to the present invention.

(X) inhibiting proliferation and differentiation of hematopoietic stem cells by culturing the hematopoietic stem cells in a medium containing a sonicated liquid component of cord blood (Y) accelerating proliferation of the hematopoietic stem cells by culturing the hematopoietic stem cells in a medium containing a non-sonicated liquid component of cord blood In the present invention, the medium used in the acceleration step is not particularly limited, and preferably is a medium containing a liquid component, for example. The liquid component contained in the medium is not particularly limited, and examples thereof include human cord blood serum, fetal bovine serum, and human peripheral blood serum. The liquid component preferably is, for example, a non-sonicated liquid component, more preferably a non-sonicated liquid component of cord blood as used in the above-described step (Y), and particularly preferably an untreated liquid component derived from the same cord blood as the hematopoietic stem cells.

In the present invention, either the inhibition step or the proliferation acceleration step may be performed first, as in the control method according to the present invention. The production method according to a first embodiment is such that, for example, first, the hematopoietic stem cells are inoculated into a medium containing the treated liquid component and proliferation and differentiation of the hematopoietic stem cells are inhibited until a desired time at which the proliferation of the hematopoietic stem cells is started, and proliferation of the hematopoietic stem cells is started at the desired time. The production method according to a second embodiment is such that, for example, first, the hematopoietic stem cells are proliferated, and then the proliferated hematopoietic stem cells are inoculated into a medium containing the treated liquid component to inhibit the proliferation and differentiation of the hematopoietic stem cells until a desired time at which the hematopoietic stem cells are used. It is possible to switch between the inhibition of the proliferation and differentiation and the acceleration of the proliferation by, for example, replacing the medium containing the treated liquid component and the medium containing the untreated liquid component depending on the purpose of the control, as in the case of the above-described control method according to the present invention, for example.

In the present invention, it is preferable to use hematopoietic stem cells and a liquid component derived from cord blood of the same individual, for example, as in the above-described control method. Specifically, it is preferable to inhibit the proliferation and differentiation using hematopoietic stem cells and a treated liquid component derived from cord blood of the same individual, and then accelerate the proliferation using an untreated liquid component derived from cord blood of the same individual. The individual is not particularly limited, and examples thereof include humans and mammals excluding humans.

<Proliferation-Controlling Agent>

The proliferation-controlling agent according to the present invention is for use in the control method according to the present invention. The proliferation-controlling agent contains:

(a) a proliferation inhibitor for inhibiting proliferation and differentiation of the hematopoietic stem cells, containing a sonicated liquid component of cord blood.

It is only necessary that the proliferation-controlling agent according to the present invention contains the sonicated cord blood serum, and other configurations are by no means limited. The proliferation-controlling agent according to the present invention also can be used in the method for producing cord blood hematopoietic stem cells according to the present invention, for example.

The proliferation-controlling agent according to the present invention further may contain a proliferation accelerator (b) shown below. The proliferation inhibitor (a) and the proliferation accelerator (b) exhibit opposite effects, i.e., inhibition and acceleration. Thus, they are contained in a proliferation-controlling agent separately as independent agents, for example.

(b) a proliferation accelerator for accelerating proliferation of hematopoietic stem cells, containing a non-sonicated liquid component of cord blood In the proliferation-controlling agent according to the present invention, it is preferable that the liquid component in the proliferation inhibitor and the liquid component in the proliferation accelerator are derived from cord blood of the same individual. In the proliferation-controlling agent according to the present invention, the treated liquid component in the proliferation inhibitor and the untreated liquid component in the proliferation accelerator are the same as described above, unless otherwise stated.

<Proliferation-Controlling Kit>

The proliferation-controlling kit according to the present invention is for use in the control method according to the present invention. The proliferation-controlling kit includes:

(a) a proliferation inhibitor for inhibiting proliferation and differentiation of the hematopoietic stem cells, containing a sonicated liquid component of cord blood.

It is only necessary that the proliferation-controlling kit according to the present invention includes the proliferation inhibitor, and the proliferation inhibitor is the same as that used in the proliferation-controlling agent according to the present invention. The proliferation-controlling kit according to the present invention also can be used in the method for producing cord blood hematopoietic stem cells according to the present invention, for example.

The proliferation-controlling kit according to the present invention further may include a proliferation accelerator (b) shown below, for example. By including the proliferation accelerator, the proliferation-controlling kit easily can accelerate the proliferation and inhibit the proliferation and differentiation of the cord blood hematopoietic stem cells. The proliferation accelerator is the same as that used in the proliferation-controlling agent according to the present invention.

(b) a proliferation accelerator for accelerating proliferation of hematopoietic stem cells, containing a non-sonicated liquid component of cord blood.

In the proliferation-controlling kit according to the present invention, the proliferation inhibitor and the proliferation accelerator preferably are contained in different containers, because they are used for opposite purposes.

<Cord Blood Component Preparation Device>

The cord blood component preparation device according to the present invention is a device for preparing cord blood hematopoietic stem cells, a sonicated liquid component of cord blood, and a non-sonicated liquid component of cord blood from the same cord blood, for use in the control method or the production method according to the present invention. According to the cord blood component preparation device of the present invention, cord blood hematopoietic stem cells to be controlled, a liquid component for inhibiting the proliferation and differentiation, and a liquid component for accelerating the proliferation can be prepared using this device alone. First to fourth cord blood component preparation devices according to the present invention will be described below.

The first cord blood component preparation device of the present invention includes:
a storage unit for storing cord blood;
an erythrocyte accommodation unit for accommodating erythrocytes;
a hematopoietic stem cell accommodation unit for accommodating hematopoietic stem cells;
first and second plasma accommodation units for accommodating plasma; and
first and second serum accommodation units for accommodating serum.

In the first cord blood component preparation device, the storage unit is connected to each of the erythrocyte accommodation unit, the hematopoietic stem cell accommodation unit, and the first and second plasma accommodation units,
the first plasma accommodation unit is connected to the first serum accommodation unit,
the second plasma accommodation unit is connected to the second serum accommodation unit,
the storage unit is configured so that an erythrocyte sedimenting agent can be introduced thereto,
the erythrocyte accommodation unit is configured so that erythrocytes having sedimented from cord blood in the storage unit can be introduced thereto,
the hematopoietic stem cell accommodation unit is configured so that hematopoietic stem cells having sedimented from a supernatant obtained after the sedimentation of the erythrocytes in the storage unit can be introduced thereto,
the first plasma accommodation unit and the second plasma accommodation unit are configured so that the supernatant obtained after the sedimentation of the erythrocytes and the supernatant obtained after the sedimentation of the hematopoietic stem cells in the storage unit can be introduced thereto, respectively,
the first plasma accommodation unit is configured so that sonication and a fibrin-forming treatment with respect to the supernatant introduced thereto can be performed therein,
the first serum accommodation unit is configured so that, among a sediment fraction and a supernatant fraction obtained from the supernatant after being subjected to the sonication and the fibrin-forming treatment in the first plasma accommodation unit, the supernatant fraction can be introduced thereto as sonicated serum,
the second plasma accommodation unit is configured so that a fibrin-forming treatment with respect to the supernatant introduced thereto can be performed therein, and
the second serum accommodation unit is configured so that, among a sediment fraction and a supernatant fraction obtained from the supernatant after being subjected to the fibrin-forming treatment in the second plasma accommodation unit, the supernatant fraction can be introduced thereto as non-sonicated serum.

The second cord blood component preparation device of the present invention includes:
a storage unit for storing cord blood;
a cell-containing plasma accommodation unit for accommodating plasma containing hematopoietic stem cells;
a hematopoietic stem cell accommodation unit for accommodating hematopoietic stem cells;
first and second plasma accommodation units for accommodating plasma; and
first and second serum accommodation units for accommodating serum.

In the second cord blood component preparation device, the storage unit is connected to the cell-containing plasma accommodation unit,
the cell-containing plasma accommodation unit is connected to each of the hematopoietic stem cell accommodation unit and the first and second plasma accommodation units,
the first plasma accommodation unit is connected to the first serum accommodation unit,
the second plasma accommodation unit is connected to the second serum accommodation unit,
the storage unit is configured so that an erythrocyte sedimenting agent can be introduced thereto,
the cell-containing plasma accommodation unit is configured so that, among a sediment fraction containing erythrocytes having sedimented from cord blood in the storage unit and a supernatant fraction, the supernatant fraction can be introduced thereto as plasma containing hematopoietic stem cells,
the hematopoietic stem cell accommodation unit is configured so that hematopoietic stem cells having sedimented from the plasma containing hematopoietic stem cells in the cell-containing plasma accommodation unit can be introduced thereto,
the first plasma accommodation unit and the second plasma accommodation unit are configured so that a supernatant obtained after removing the hematopoietic stem cells in the cell-containing plasma accommodation unit can be introduced thereto,
the first plasma accommodation unit is configured so that sonication and a fibrin-forming treatment with respect to the supernatant introduced thereto can be performed therein,
the first serum accommodation unit is configured so that, among a sediment fraction and a supernatant fraction obtained from the supernatant after being subjected to the sonication and the fibrin-forming treatment in the first plasma accommodation unit, the supernatant fraction can be introduced thereto as sonicated serum,
the second plasma accommodation unit is configured so that a fibrin-forming treatment with respect to the supernatant introduced thereto can be performed therein, and
the second serum accommodation unit is configured so that, among a sediment fraction and a supernatant fraction obtained from the supernatant after being subjected to the fibrin-forming treatment in the second plasma accommodation unit, the supernatant fraction can be introduced thereto as non-sonicated serum.

The third cord blood component preparation device of the present invention includes:
a storage unit for storing cord blood;
a cell-containing plasma accommodation unit for accommodating plasma containing hematopoietic stem cells;
first and second plasma accommodation units for accommodating plasma; and
first and second serum accommodation units for accommodating serum.

In the third cord blood component preparation device, the storage unit is connected to the cell-containing plasma accommodation unit,
the cell-containing plasma accommodation unit is connected to each of the first and second plasma accommodation units,
the first plasma accommodation unit is connected to the first serum accommodation unit,
the second plasma accommodation unit is connected to the second serum accommodation unit,
the storage unit is configured so that an erythrocyte sedimenting agent can be introduced thereto,
the cell-containing plasma accommodation unit is configured so that, among a sediment fraction containing erythrocytes having sedimented from cord blood in the storage unit and a supernatant fraction, the supernatant fraction can be introduced thereto as a plasma fraction containing hematopoietic stem cells, and after the plasma fraction introduced thereto is separated into a sediment fraction containing the hematopoietic stem cells and a supernatant fraction, the cell-containing plasma accommodation unit can be divided into a lower region containing the sediment fraction and an upper region containing the supernatant fraction, the lower region of the cell-containing plasma accommodation unit serves as a hematopoietic stem cell accommodation unit, the first plasma accommodation unit and the second plasma accommodation unit are configured so that the supernatant fraction in the upper region of the cell-containing plasma accommodation unit can be introduced thereto, the first plasma accommodation unit is configured so that sonication and a fibrin-forming treatment with respect to the supernatant introduced thereto can be performed therein, the first serum accommodation unit is configured so that, among a sediment fraction and a supernatant fraction obtained from the supernatant after being subjected to the sonication and the fibrin-forming treatment in the first plasma accommodation unit, the supernatant fraction can be introduced thereto as a sonicated serum fraction, the second plasma accommodation unit is configured so that a fibrin-forming treatment with respect to the supernatant introduced thereto can be performed therein, and the second serum accommodation unit is configured so that, among a sediment fraction and a supernatant fraction obtained from the supernatant after being subjected to the fibrin-forming treatment in the second plasma accommodation unit, the supernatant fraction can be introduced thereto as non-sonicated serum.

The fourth cord blood component preparation device of the present invention includes:

first and second storage units for storing cord blood;

an erythrocyte accommodation unit for accommodating erythrocytes;

a hematopoietic stem cell accommodation unit for accommodating hematopoietic stem cells;

first and second plasma accommodation units for accommodating plasma; and first, second, and third serum accommodation units for accommodating serum.

In the fourth cord blood component preparation device, the first storage unit is connected to each of the erythrocyte accommodation unit, the hematopoietic stem cell accommodation unit, and the first and second plasma accommodation units, the first plasma accommodation unit is connected to the first serum accommodation unit, the second plasma accommodation unit is connected to the second serum accommodation unit, the first storage unit is configured so that an anticoagulant and an erythrocyte sedimenting agent can be introduced thereto, the erythrocyte accommodation unit is configured so that erythrocytes having sedimented from cord blood in the storage unit can be introduced thereto, the hematopoietic stem cell accommodation unit is configured so that hematopoietic stem cells having sedimented from a supernatant obtained after the sedimentation of the erythrocytes in the storage unit can be introduced thereto, the first plasma accommodation unit and the second plasma accommodation unit are configured so that the supernatant obtained after the sedimentation of the erythrocytes and the supernatant obtained after the sedimentation of the hematopoietic stem cells in the storage unit can be introduced thereto, respectively, the first plasma accommodation unit is configured so that sonication and a fibrin-forming treatment with respect to the supernatant introduced thereto can be performed therein, the first serum accommodation unit is configured so that, among a sediment fraction and a supernatant fraction obtained from the supernatant after being subjected to the sonication and the fibrin-forming treatment in the first plasma accommodation unit, the supernatant fraction can be introduced thereto as sonicated serum, the second plasma accommodation unit is configured so that a fibrin-forming treatment with respect to the supernatant introduced thereto can be performed therein, the second serum accommodation unit is configured so that, among a sediment fraction and a supernatant fraction obtained from the supernatant after being subjected to the fibrin-forming treatment in the second plasma accommodation unit, the supernatant fraction can be introduced thereto as non-sonicated serum, the second storage unit is connected to the third serum accommodation unit;

the second storage unit is configured so that a blood coagulation-accelerating substance for accelerating blood coagulation can be introduced thereto, and the third serum accommodation unit is configured so that a supernatant fraction obtained after blood coagulation in the second storage unit can be introduced thereto.

In the present invention, it is preferable that the storage unit and the respective accommodation units are connected to each other in an airtight manner. This allows the inside of the device of the present invention to be kept sterile, for example, and a series of operations subsequent to the introduction of cord blood can be carried out without exposing the cord blood to the outside air, for example. Furthermore, by connecting the storage unit and the respective accommodation units in an airtight manner, they also can be kept in a liquid-tight state, for example.

It is preferable that the storage unit and the respective accommodation units are formed of a flexible material, for example. Examples of the flexible material include: polyolefins such as polyethylene, polypropylene, polytetrafluoroethylene, and polybutylene terephthalate; polyvinyl chlorides such as soft polyvinyl chloride; polyvinyl alcohols; ethylene-vinyl acetate copolymer resin; silicone; polyurethane; and resins such as nylon. Furthermore, it is preferable that the cord blood component preparation device according to the present invention can be sterilized, for example, from a hygiene viewpoint, and, as will be described below, the respective plasma accommodation units may be subjected to a heat treatment as the fibrin-forming treatment, for example. Thus, the flexible material preferably has heat resistance.

The fibrin-forming treatment in the first plasma accommodation unit and the second plasma accommodation unit is not particularly limited, and examples thereof include: a heat treatment to the plasma accommodation units; and introduction of a blood coagulation reagent to the plasma accommodation units. In the former case, the respective plasma accommodation units may be configured so that a heat treatment to the supernatant introduced thereto can be performed, for example. In the latter case, the respective plasma accommodation units may be configured so that the blood coagulation reagent can be introduced thereto, for example. The blood coagulation reagent may be accommodated in the respective plasma accommodation units in advance, or may be introduced to the respective plasma accommodation units when used, for example. The fibrin-forming treatment in the first and second plasma accommodation units of the present invention preferably is a heat treatment, for example.

The form of the storage unit and the respective accommodation units is not particularly limited. Preferably, they are in the form of bag from the aspect of excellent handleability, for example. The bag can be formed by, for example, laminating two flexible resin sheets and then bonding an edge portion (seal portion) as the rim of the laminate. The type of the bonding is not particularly limited, and examples thereof include: welding such as heat-sealing and ultrasonic welding; and adhesion using an adhesive or the like.

The size of the storage unit and the respective accommodation units is not particularly limited. The capacity of the storage unit preferably is 50 to 400 ml, for example, and the amount of cord blood to be introduced to the storage unit preferably is 40 to 80 vol % of the capacity of the storage unit, for example. The capacities of the respective accommodation units can be determined as appropriate depending on, for example, the amount of cord blood that can be introduced to the storage unit. It preferably is 25 to 200 ml, and preferably is 30 to 70 vol % of the capacity of the storage unit. The storage unit and the respective accommodation units may contain air inside, for example. However, it is preferable that the content of the air is as small as possible. In the fourth cord blood component preparation device, the capacity of the first storage unit is the same as described above, for example, and the capacity of the second storage unit preferably is 10 to 80 vol %, for example, and the amount of cord blood to be introduced to the second storage unit preferably is 40 to 80 vol % of the capacity of the second storage unit, for example.

It is preferable that the storage unit and the respective accommodation units are connected to each other through tubes, for example. The tubes preferably are formed of a flexible material, for example. Furthermore, as will be described below, it is preferable that the hematopoietic stem cell accommodation unit 12, the first serum accommodation unit 13b, and the second serum accommodation unit 14b are detached from the cord blood component preparation device in the state where the flow paths of the tubes are blocked. Thus, the tubes preferably are formed of a material that can be cut and fused by heating and melting, for example. Examples of such a material include: polyolefins such as polyethylene, polypropylene, polytetrafluoroethylene, and polybutylene terephthalate; polyvinyl chloride such as soft polyvinyl chloride; polyvinyl alcohols; ethylene-vinyl acetate copolymer resins; silicone; polyurethane; and nylon. Preferably, the cord blood component preparation device of the present invention further includes a member that can block and unblock the flow path of a tube as appropriate, for example. Examples of the member include clamping members such as a clamp and forceps. By pinching each tube with the clamping member as appropriate, it is possible to switch the flow path between the storage unit and the respective accommodation units and between the respective accommodation units. Furthermore, as the member that opens/closes the flow path, it is also possible to use a valve or the like, for example. The valve may be disposed at a certain point on the tube, for example, or may be provided at a branched portion of the tubes, which will be described below. Furthermore, a branch connector to be described below also may serve as a valve.

In the first and third cord blood component preparation devices, for example, when cord blood is introduced to the storage unit directly from a patient, the storage unit further may contain an anticoagulant or may be configured so that the anticoagulant can be introduced thereto. In the latter case, for example, it is preferable to introduce the anticoagulant to the storage unit before introducing cord blood to the storage unit. The anticoagulant is not particularly limited, and examples thereof include a CPD solution (Citrate-Phosphate-Dextrose solution) and an ACD-A solution (Acid-Citrate-Dextrose-A solution). The amount of the anticoagulant is not particularly limited, and can be determined depending on the volume of the storage unit, the volume of the cord blood to be introduced to the storage unit, and the like, for example. The amount of the anticoagulant to be added preferably is 30 to 100 vol % of cord blood to be introduced, for example. In the fourth cord blood component preparation device, an anticoagulant can be introduced to the first storage unit as described above, and it is not necessary to introduce an anticoagulant to the second storage unit.

In the first to third cord blood component preparation devices, an erythrocyte sedimenting agent may be accommodated in the storage unit in advance, or an erythrocyte sedimenting agent may be introduced to the storage unit from the outside, for example. For example, in the case where cord blood containing an erythrocyte sedimenting agent is introduced to the storage unit, it is not necessary that the erythrocyte sedimenting agent is accommodated in or introduced to the storage unit.

The cord blood component preparation device according to the present invention can be used for preparing components not only from human cord blood but also from cord blood of mammals such as rodents, domestic animals, and primates, for example.

First Embodiment

Next, an example of the first cord blood component preparation device according to the present invention will be described with reference to FIG. 1. It is to be noted, however, the present invention is not limited thereto.

FIG. 1 is a plan view schematically showing the cord blood component preparation device of the present embodiment. The cord blood component preparation device 1 includes: a storage unit 10 for storing cord blood; an erythrocyte accommodation unit 11 for accommodating erythrocytes; a hematopoietic stem cell accommodation unit 12 for accommodating hematopoietic stem cells; a first plasma accommodation unit 13a and a second plasma accommodation unit 14a for accommodating plasma; and a first serum accommodation unit 13b and a second serum accommodation unit 14b for accommodating serum. In the storage unit 10 and the respective accommodation units 11 to 14b shown in FIG. 1, the inside of the dotted line is a space capable of accommodating the respective components, and the portion between the dotted line and the solid line indicating the outer frame is a seal portion. The storage unit 10 has two inlets 15a and 15b and two outlets 16c and 16f. The left inlet 15a of the storage unit 10 is an inlet for cord blood, and one end of a tube 18a is connected thereto. The other end of the tube 18a is a connection part 9 to a cord blood bag. For example, a puncture needle or the like can be connected thereto, and the connection part 9 is covered with a cap or the like until it is used. The right inlet 15b of the storage unit 10 is an inlet for an erythrocyte sedimenting agent, and one end of a tube 18b is connected thereto. The other end of the tube 18b is a connection part 9 to a container of an erythrocyte sedimenting agent, and the connection part 9 is covered with a cap or the like until it is used. The lower outlet 16c of the storage unit 10 is an outlet for erythrocytes and hematopoietic stem cells having sedimented from the cord blood, and one end of a tube 18c is connected thereto. The upper outlet 16f is an outlet for plasma obtained after removing the erythrocytes and the hematopoietic stem cells, and one end of a tube 18f is connected thereto. The erythrocyte accommodation unit 11 has an inlet 15d for the erythrocytes having sedimented from the cord blood, and one end of a tube 18d is connected to the inlet 15d. The hematopoietic stem cell accommodation unit 12 has an inlet 15e for the hematopoietic stem cells having sedimented from the cord blood, and one end of a tube 18e is connected to the inlet 15e. The tube 18c connected to the storage unit 10, the tube 18d connected to the erythrocyte accommodation unit 11, and the tube 18e connected to the hematopoietic stem cell accommodation unit 12 communicate with each other with the other ends thereof being connected to each other via a branch connector 19. The first plasma accommodation unit 13a has an inlet 15g for the plasma obtained after removing the erythrocytes and the hematopoietic stem cells and an outlet 16i for serum. One end of a tube 18g is connected to the inlet 15g, and one end of a tube 18i is connected to the outlet 16i. On the other hand, the second plasma accommodation unit 14a also has an inlet 15h for the plasma obtained after removing the erythrocytes and the hematopoietic stem cells and an outlet 16k for serum. One end of a tube 18h is connected to the inlet 15h, and one end of a tube 18k is connected to the outlet 16k. The tube 18f connected to the storage unit 10, the tube 18g connected to the first plasma accommodation unit 13a, and the tube 18h connected to the second plasma accommodation unit 14a communicate with each other with the other ends thereof being connected to each other via another branch connector 19. The first serum accommodation unit 13b has an inlet 15i for the serum, and the other end of the tube 18i connected to the first plasma accommodation unit 13a is connected to the inlet 15i. The second serum accommodation unit 14b has an inlet 15k for the serum, and the other end of the tube 18k connected to the second plasma accommodation unit 14a is connected to the inlet 15k.

The cord blood component preparation device 1 preferably has clamping members (not shown), such as clamps, for clamping the tubes, for example. Preferably, the tubes connecting the storage unit 10 to the respective accommodation units 11, 12, 13a, and 14a, and the tubes connecting the plasma accommodation units 13a and 14a to the serum accommodation units 13b and 14b are provided with the clamping members, for example. With the use of the clamping members, switching to a desired flow path becomes possible.

Between the first plasma accommodation unit 13a and the first serum accommodation unit 13b (e.g., the tube 18i) and between the second plasma accommodation unit 14a and the second serum accommodation unit 14b (e.g., the tube 18k), filters for removing remaining erythrocytes and the like may be present, for example. Such a filter may be present also in the tube 18h connected to the second plasma accommodation unit 14a.

Each of the accommodation units may have an openable outlet 17, for example. For example, when separating various components of the cord blood, the opening of the outlet 17 preferably is closed as shown in FIG. 1. Then, when discharging the various components accommodated in the respective accommodation units to the outside, the components inside can be discharged through the outlet 17 opened by removing the closed portion. Also, by inserting a collection needle into the closed outlet 17, the components inside can be discharged through the collection needle, for example.

A method for preparing hematopoietic stem cells, sonicated serum (treated serum), and non-sonicated serum (untreated serum) from cord blood using the cord blood component preparation device 1 of the present embodiment will be described with reference to an illustrative example. Specific treatment conditions can be set to be the same as those described above, unless otherwise stated.

First, cord blood is provided. In the case of human cord blood, it is available in the state of being accommodated in a blood bag, for example. Human cord blood accommodated in a blood bag generally contains an anticoagulant. To this blood bag, one end of the tube 18a connected to the storage unit 10 is connected, and the cord blood is introduced to the storage unit 10. A blood collection needle may be attached to the connection part 9 provided at the tip of the tube 18a, and the cord blood may be introduced to the storage unit 10 by inserting the blood collection needle into the blood bag, for example. At this time, in order to prevent the cord blood in the storage unit 10 from flowing into the tubes 18c, 18d, and 18e, the erythrocyte accommodation unit 11, and the hematopoietic stem cell accommodation unit 12 via the lower outlet 16c, it is preferable to block a flow path of the tube 18c with a clamp in the vicinity of the storage unit 10. After the cord blood is introduced to the storage unit 10, the tip of the tube 18a for cord blood introduction may be covered with a cap, or a desired portion of the tube 18a may be cut and fused using a sealer or the like, for example. Also, cord blood may be collected directly from a patient through the blood collection needle attached to the tip of the tube 18a and stored in the storage unit 10. When cord blood is collected directly from a patient and stored in the storage unit 10 as described above, an anticoagulant may be accommodated in the storage unit 10 in advance, for example. Alternatively, prior to the introduction of cord blood, an anticoagulant may be introduced to the storage unit 10 through the tube 18b connected to the storage unit 10, for example.

Subsequently, an erythrocyte sedimenting agent is introduced to the storage unit 10 through the tube 18b connected to the storage unit 10, and the cord blood is mixed with the erythrocyte sedimenting agent. Thereafter, the storage unit 10 was allowed to stand still. Then, after the cord blood has separated into an erythrocyte fraction and a supernatant fraction in the storage unit 10, the erythrocyte fraction having sedimented is introduced to the erythrocyte accommodation unit 11 through the tubes 18c and 18d under the storage unit 10. At this time, in order to prevent the erythrocyte fraction from being introduced to the hematopoietic stem cell accommodation unit 12, it is preferable to block the flow path of the tube 18e connected to the hematopoietic stem cell accommodation unit 12 with a clamp in the vicinity of the branch connector 19 and then release the blocking of the flow path of the tube 18c with the clamp. This opens the flow path extending from the storage unit 10 to the erythrocyte accommodation unit 11, thereby allowing the erythrocyte fraction to be introduced to the erythrocyte accommodation unit 11. After the erythrocyte fraction is introduced to the erythrocyte accommodation unit 11, it is preferable to block the flow: path of the tube 18c again with a clamp in the vicinity of the storage unit 10.

After the erythrocyte fraction is discharged in the above described manner, the storage unit 10 is centrifuged, thus achieving the separation into a sediment fraction containing hematopoietic stem cells and a supernatant fraction containing plasma. At this time, conditions for the centrifugation are as described above.

Then, through the tubes 18c and 18e under the storage unit 10, the hematopoietic stem cell fraction having sedimented is introduced to the hematopoietic stem cell accommodation unit 12. At this time, in order to prevent the hematopoietic stem cell fraction from being introduced to the erythrocyte accommodation unit 11, it is preferable to block the flow path of the tube 18d connected to the erythrocyte accommodation unit 11 with a clamp in the vicinity of the branch connector 19 and then release the blocking of the flow path of the tube 18c with the clamp. After the hematopoietic stem cell fraction is introduced to the hematopoietic stem cell accommodation unit 12, it is preferable to block the flow path of the tube 18c again with a clamp in the vicinity of the storage unit 10. Alternatively, a desired portion of the tube 18c or the inlet 15e may be cut and fused using a sealer or the like. By this operation; a sealed hematopoietic stem cell-accommodating bag accommodating the hematopoietic stem cell fraction is obtained from the cord blood component preparation device 1. The hematopoietic stem cells in the bag can be taken out from the bag by cutting off the blocked portion of the outlet 17 or piercing the blocked outlet 17 with a collection needle, for example.

On the other hand, the plasma fraction remaining in the storage unit 10 is dispensed to the first plasma accommodation unit 13a and the second plasma accommodation unit 14a through the tubes 18f, 18g, and 18h. When introducing the plasma fraction to the first plasma accommodation unit 13a and then to the second plasma accommodation unit 14a, it is preferable to introduce the plasma fraction to the first plasma accommodation unit 13a with the flow path of the tube 18h connected to the second plasma accommodation unit 14a being blocked in the vicinity of the branch connector 19, then block the flow path of the tube 18g connected to the first plasma accommodation unit 13a in the vicinity of the branch connector 19, and thereafter, to release the blocking of the flow path of the tube 18h with the clamp, thereby allowing the plasma fraction to be introduced to the second plasma accommodation unit 14a, for example.

Next, the first plasma accommodation unit 13a is subjected to sonication. The sonication can be carried out by immersing the plasma accommodation unit and an oscillator in a liquid in a bath and causing the oscillator to output ultrasonic waves, for example. Subsequently, the first plasma accommodation unit 13a is subjected to a heat treatment. By this heat treatment, fibrin is formed from fibrinogen in the plasma fraction. The heat treatment can be carried out by immersing the first plasma accommodation unit 13a in a heated liquid in a bath, for example. The first plasma accommodation unit 13a after being subjected to the heat treatment is centrifuged, thus achieving the separation into a sediment fraction containing the formed fibrin, platelets, and the like and a supernatant fraction containing serum. This supernatant fraction is introduced to the first serum accommodation unit 13b through the tube 18i connecting the first plasma accommodation unit 13a to the first serum accommodation unit 13b. In this manner, the sonicated serum can be collected. When introducing the supernatant fraction in the first plasma accommodation unit 13a to the first serum accommodation unit 13b, it is preferable to prevent the sediment fraction from entering the first serum accommodation unit 13b. In this case, examples of the method of preventing this include pinching the boundary between the supernatant fraction and the sediment fraction with a clamp or the like from the outside of the first plasma accommodation unit 13a so as to separate the supernatant fraction and the sediment fraction.

On the other hand, the second plasma accommodation unit 14a is subjected to a heat treatment in the same manner as in the above, except that the second plasma accommodation unit 14a is not subjected to sonication and that platelets are removed. The heat treatment of the second plasma accommodation unit 14a may be performed at the same time as the heat treatment of the first plasma accommodation unit 13a, for example. Subsequently, the second plasma accommodation unit 14a after being subjected to the heat treatment is centrifuged, thus achieving the separation into a sediment fraction containing the formed fibrin, platelets, and the like and a supernatant fraction containing serum. This supernatant fraction is introduced to the second serum accommodation unit 14b through the tube 18k connecting the second plasma accommodation unit 14a to the second serum accommodation unit 14b. In this manner, non-sonicated serum can be collected.

With regard to the first serum accommodation unit 13b and the second serum accommodation unit 14b, a desired portion of the tube 18i or the inlet 15i and a desired portion of the tube 18k or the inlet 15k may be cut and fused using a sealer or the like, for example. By this operation, a sealed serum-accommodating bag in which the treated serum is accommodated and a sealed serum-accommodating bag in which the untreated serum is accommodated can be obtained from the cord blood component preparation device 1. The serum in each of the bags can be taken out from the bag by cutting off the blocked portion of the outlet 17 or piercing the blocked outlet 17 with a collection needle, for example.

The hematopoietic stem cell bag accommodating the hematopoietic stem cells, serum bag accommodating the treated serum, and serum bag accommodating the untreated serum obtained in the above-described manner can be preserved by cryopreservation or the like before use, for example. When preserving them by cryopreservation, after the hematopoietic stem cell accommodation unit 12, the first serum accommodation unit 13b, and the second serum accommodation unit 14b have accommodated the components to be accommodated therein, respectively, a cryoprotectant may be introduced to these units through any of the tubes connected thereto and then the tubes may be cut off and fused, for example.

Furthermore, in the embodiment of the present invention, when removing fibrinogen from plasma and collecting serum as described above, it is possible to utilize the activation mechanism of a blood coagulation system instead of the heat treatment. In this case, it is preferable that, after the first plasma accommodation unit 13a is subjected to sonication in a manner described above, a blood coagulation reagent further is added to the first plasma accommodation unit 13a. Examples of the blood coagulation reagent include the above-described coagulation factor such as thrombin. When the cord blood contains an anticoagulant, it is preferable that the blood coagulation reagent further contains a neutralizer such as calcium chloride, for example. By adding the blood coagulation reagent as described above, fibrin is formed from fibrinogen in plasma, so that the fibrinogen can be removed by carrying out centrifugation out thereafter in the same manner as in the above. The blood coagulation reagent may be added by adding a coagulation factor such as thrombin and a neutralizer to the plasma at the same time, or by adding the coagulation factor after adding the neutralizer, for example. In such an aspect of the invention, it is preferable that the first plasma accommodation unit 13a has an inlet for the blood coagulation reagent. The inlet preferably is configured so that, for example, one end of a tube is connected thereto and the other end of the tube serves as a connection part to an accommodation unit for the blood coagulation reagent, which is covered with a cap or the like before use. Furthermore; it is also preferable to add the blood coagulation reagent to the second plasma accommodation unit 14a, instead of subjecting the second plasma accommodation unit 14a to a heat treatment. It is also preferable that the second plasma accommodation unit 14a has an inlet for the blood coagulation reagent. The inlet preferably is configured so that, for example, one end of a tube is connected thereto and the other end of the tube serves as a connection part to an accommodation unit for the blood coagulation reagent, which is covered with a cap or the like before use.

Second Embodiment

Figure 2:
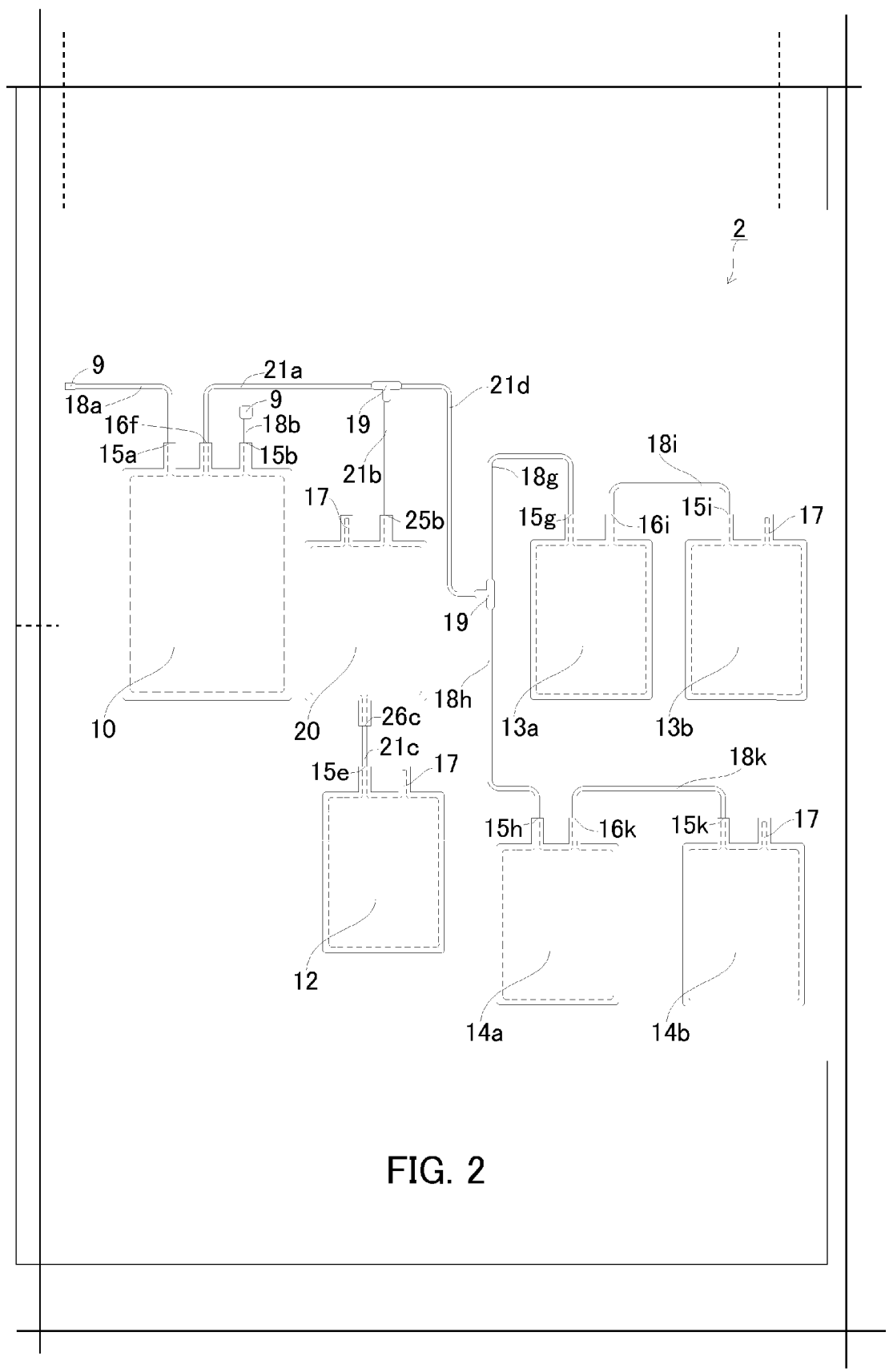
FIG. 2 is a plan view schematically showing an example of another cord blood component preparation device according to the present invention.

Next, an example of the second cord blood component preparation device according to the present invention will be described with reference to FIG. 2. In FIG. 2, elements the same as those in FIG. 1 are marked with the same reference numerals. The second cord blood component preparation device is the same as the first cord blood component preparation device, unless otherwise stated. Unless otherwise stated, the present invention is not limited thereto.

FIG. 2 is a plan view schematically showing the cord blood component preparation device of the present embodiment. The cord blood component preparation device 2 includes: a storage unit 10 for storing cord blood; a cell-containing plasma accommodation unit 20 for accommodating hematopoietic stem cell-containing plasma obtained after removing erythrocytes; a hematopoietic stem cell accommodation unit 12 for accommodating hematopoietic stem cells; a first plasma accommodation unit 13a and a second plasma accommodation unit 14a for accommodating plasma; and a first serum accommodation unit 13b and a second serum accommodation unit 14b for accommodating serum. The storage unit 10 has two inlets 15a and 15b and an outlet 16f. The left inlet 15a of the storage unit 10 is an inlet for cord blood, and one end of a tube 18a is connected thereto. The other end of the tube 18a is a connection part 9 to a cord blood bag. The right inlet 15b of the storage unit 10 is an inlet for an erythrocyte sedimenting agent, and one end of a tube 18b is connected thereto. The other end of the tube 18b is a connection part 9 to a container of an erythrocyte sedimenting agent. The upper outlet 16f of the storage unit 10 is an outlet for hematopoietic stem cell-containing plasma obtained after removing erythrocytes, and one end of a tube 21a is connected thereto. The removing cell-containing plasma accommodation unit 20 has an inlet 25b and an outlet 26c. The inlet 25b provided in the upper part is an inlet for hematopoietic stem cell-containing plasma, and one end of a tube 21b is connected thereto. The other end of the tube 21b connected to the cell-containing plasma accommodation unit 20 is connected to the other end of the tube 21a connected to the storage unit 10 and one end of a tube 21d via a branch connector 19. The other end of the tube 21d is connected to first ends of tubes 18g and 18h connected to the first plasma accommodation unit 13a and the second plasma accommodation units 14a via another branch connector 19.

The cord blood component preparation device 2 preferably has clamping members (not shown), such as clamps, for clamping the tubes, for example. Preferably, the clamping member such as described above is provided in: the tube 21a connecting the storage unit 10 and the cell-containing plasma accommodation unit 20; the tube 21d; the tube 21c connecting the cell-containing plasma accommodation unit 20 and the hematopoietic stem cell accommodation unit 12; the tubes 18g and 18h extending from the branch connector 19 and connected to the plasma accommodation units 13a and 14a, respectively; and the tubes 18i and 18k connecting the plasma accommodation units 13a and 14a to the serum accommodation units 13b and 14b, respectively, for example.

A method for preparing hematopoietic stem cells, treated serum, and untreated serum from cord blood using the cord blood component preparation device 2 of the present embodiment will be described with reference to an illustrative example. Specific treatment conditions can be set to be the same as those described above, unless otherwise stated.

The cord blood in the storage unit 10 is caused to separate into an erythrocyte fraction and a supernatant fraction in the same manner as described above, and thereafter, the supernatant fraction is introduced to the cell-containing plasma accommodation unit 20 through the tubes 21a and 21b extending from the upper part of the storage unit 10. The supernatant fraction is a plasma fraction containing hematopoietic stem cells. At this time, in order to prevent the supernatant fraction from being introduced to the plasma accommodation units 13a and 14a, it is preferable to block the flow path of the tube 21d with a clamp in the vicinity of the branch connector 19 connected to the tube 21b. Furthermore, in order to prevent the supernatant fraction introduced to the cell-containing plasma accommodation unit 20 from being discharged to the hematopoietic stem cell accommodation unit 12, it is preferable to block the flow path of the tube 21c with a clamp in the vicinity of the outlet 26c.

Next, the cell-containing plasma accommodation unit 20 is centrifuged, thus achieving the separation into a sediment fraction containing hematopoietic stem cells and a supernatant fraction containing plasma. At this time, conditions for the centrifugation preferably are set so that, as described above, platelets are contained in the supernatant fraction.

Then, through the tube 21c under the cell-containing plasma accommodation unit 20, the sediment fraction containing hematopoietic stem cells is introduced to the hematopoietic stem cell accommodation unit 12. It is preferable that, after introducing the hematopoietic stem cells, the flow path of the tube 21c connecting the cell-containing plasma accommodation unit 20 and the hematopoietic stem cell accommodation unit 12 is blocked with a clamp.

On the other hand, the plasma fraction remaining in the cell-containing plasma accommodation unit 20 is dispensed to the first plasma accommodation unit 13a and the second plasma accommodation unit 14a through the tubes 21b, 21d, 18g, and 18h. At this time, in order to prevent the plasma fraction from being discharged to the storage unit 10, it is preferable to block the flow path of the tube 21a connected to the storage unit 10 with a clamp in the vicinity of the branch connector 19. Then, the plasma dispensed to each unit is treated in the same manner as above so as to prepare serum.

Third Embodiment

Figure 3:
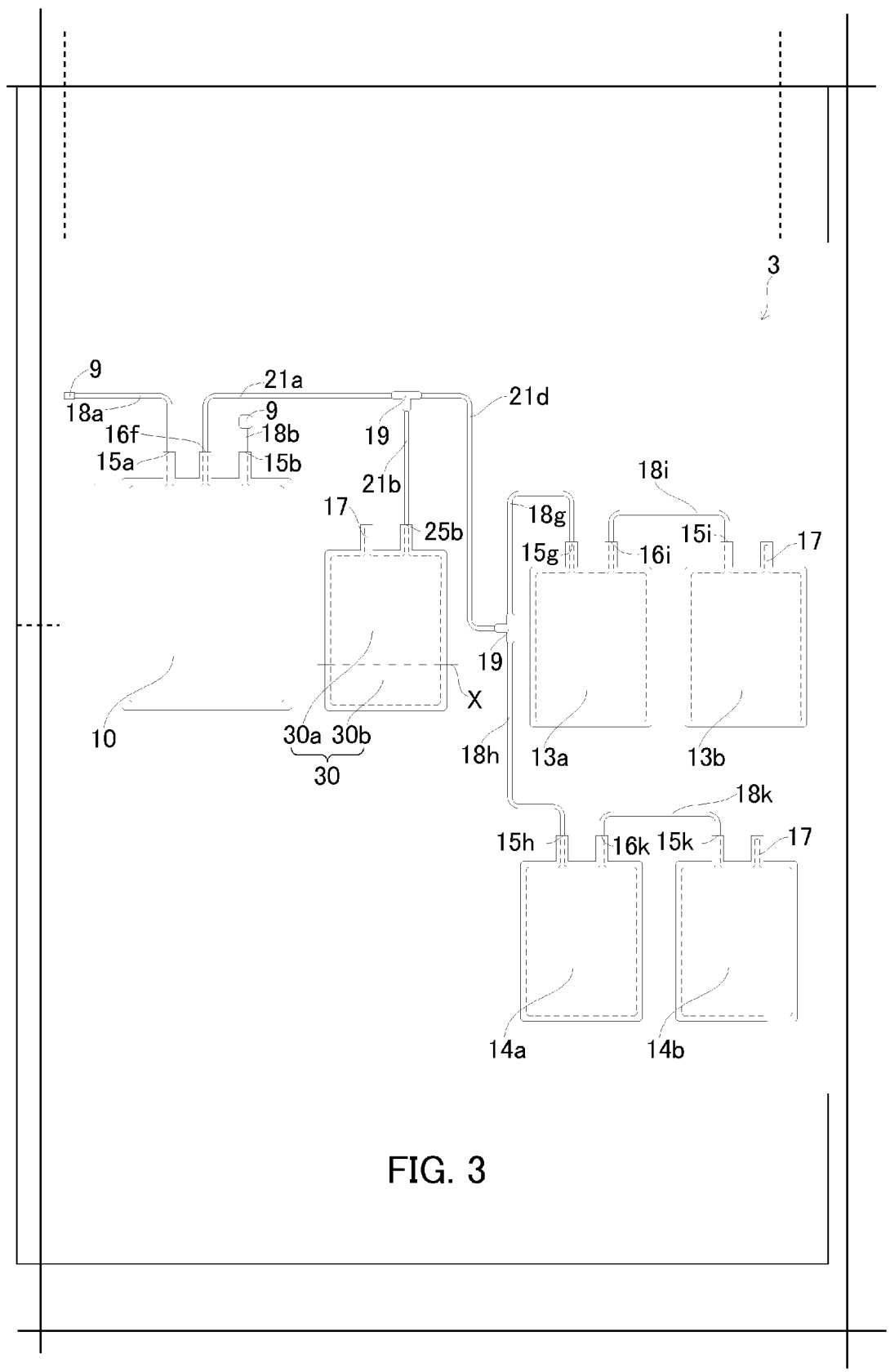
FIG. 3 is a plan view schematically showing an example of still another cord blood component preparation device according to the present invention.

Next, an example of the third cord blood component preparation device according to the present invention will be described with reference to FIG. 3. In FIG. 3, elements the same as those in FIGS. 1 and 2 are marked with the same reference numerals. The third cord blood component preparation device is the same as the first and second card blood component preparation devices, unless otherwise stated. Unless otherwise stated, the present invention is not limited thereto.

FIG. 3 is a plan view schematically showing the cord blood component preparation device of the present embodiment. The cord blood component preparation device 3 is the same as the second cord blood component preparation device described above, except that it includes, instead of the cell-containing plasma accommodation unit 20 and the hematopoietic stem cell accommodation unit 12 shown in FIG. 2, a dividable cell-containing plasma accommodation unit 30. The cell-containing plasma accommodation unit 30 is configured so that, among a sediment fraction containing erythrocytes having sedimented from cord blood and a supernatant fraction in the storage unit 10, the supernatant fraction can be introduced thereto as a plasma fraction containing hematopoietic stem cells. Furthermore, the cell-containing plasma accommodation unit 30 is configured so that, after the plasma fraction introduced thereto is caused to separate into a sediment fraction containing hematopoietic stem cells and a supernatant fraction, the space inside can be divided into a lower region 30b having the sediment fraction and an upper region 30a having the supernatant fraction.

Figure 4:
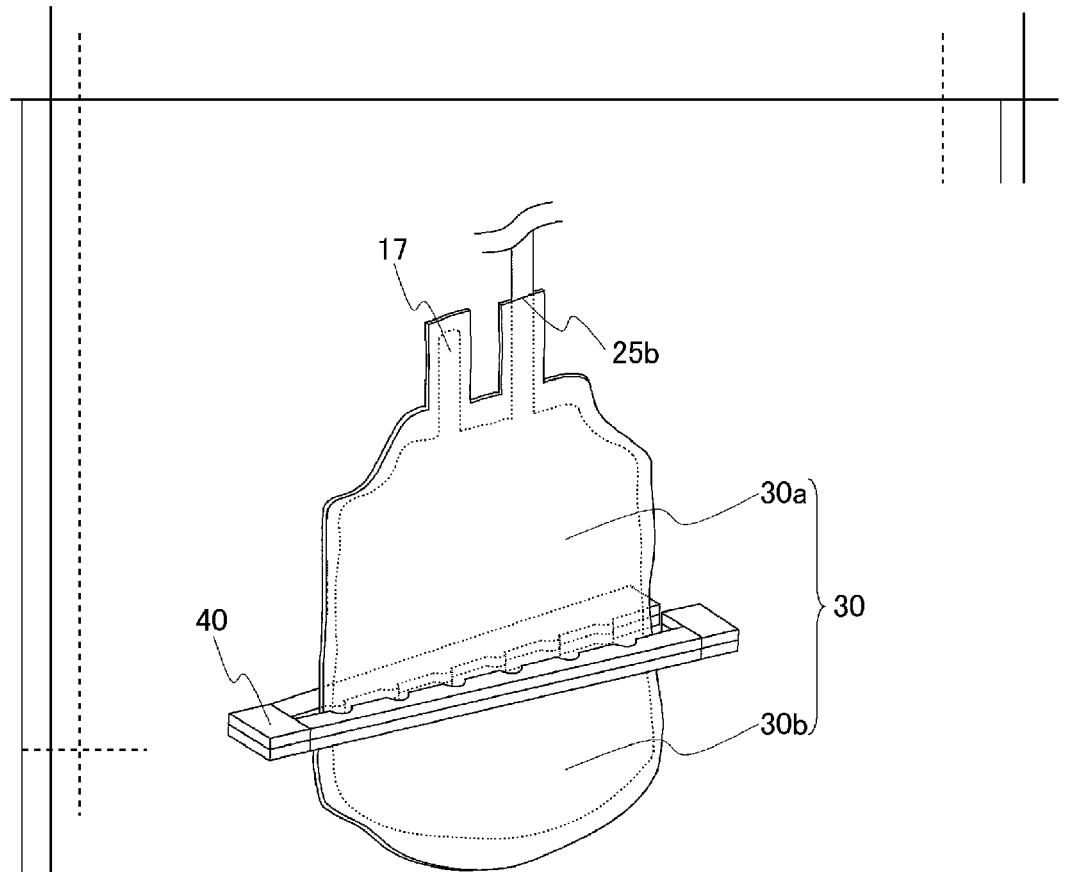
FIG. 4 is a perspective view showing an example of a method of using a cell-containing plasma accommodation unit in the cord blood component preparation device according to the present invention.

After the hematopoietic stem cell-containing plasma obtained after removing the erythrocytes is introduced to the cell-containing plasma accommodation unit 30, the cell-containing plasma accommodation unit 30 is centrifuged, thus achieving the separation into a sediment fraction containing hematopoietic stem cells and a supernatant fraction containing plasma. After the separation, the boundary between the lower region 30b having the sediment fraction and the upper region 30a having the supernatant fraction is pinched with a gripping member from the outside of the cell-containing plasma accommodation unit 30 so as to divide these regions. Specifically, as shown in FIG. 4, for example, the boundary X between the upper region 30a and the lower region 30b of the cell-containing plasma accommodation unit 30 is pinched with a clamp 40.

Then, the supernatant fraction accommodated in the upper region 30a is discharged to plasma accommodation units 13a and 14a, and serums are prepared in the same manner as above. On the other hand, the cell-containing plasma accommodation unit 30 after the supernatant fraction has been discharged therefrom (the lower region 30b) serves as an accommodation unit for hematopoietic stem cells.

Figure 5:
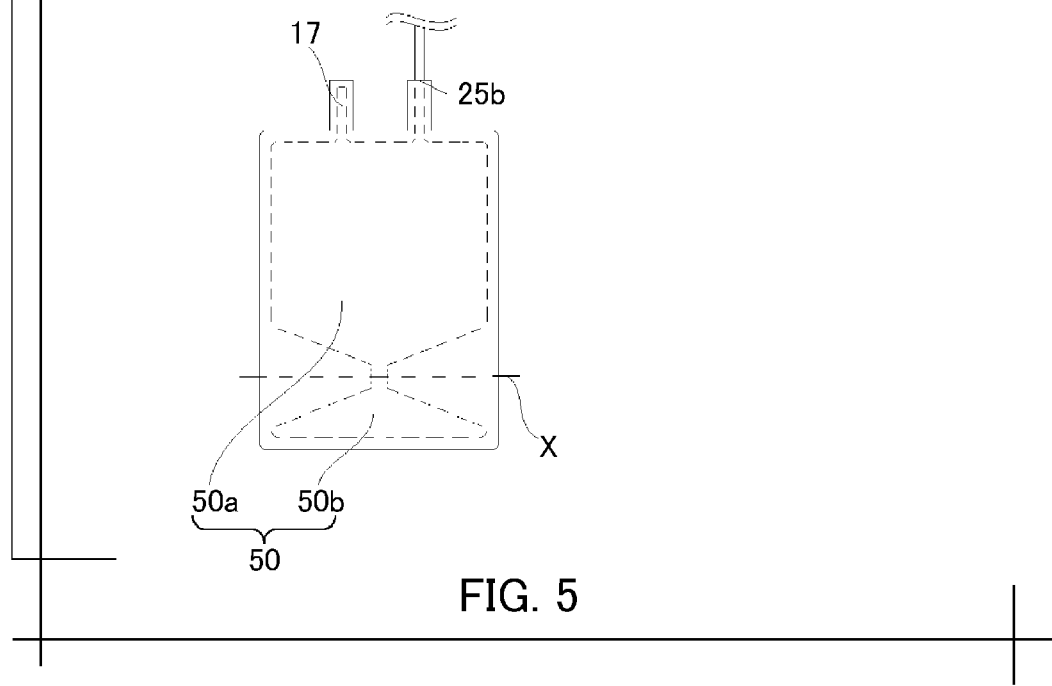
FIG. 5 is a plan view showing an example of another cell-containing plasma accommodation unit in the cord blood component preparation device according to the present invention.

In the third cord blood component preparation device 3, the cell-containing plasma accommodation unit may be a cell-containing plasma accommodation unit 50 shown in FIG. 5, for example. As shown in FIG. 5, the cell-containing plasma accommodation unit 50 is configured so that a lower part of an upper region 50a is tapered so as to allow erythrocytes having sedimented therein to move to a lower region 50b easily.

Fourth Embodiment

Next, the fourth cord blood component preparation device of the present invention will be described. The fourth cord blood component preparation device of the present invention is a device to be used when preparing the respective components by introducing uncoagulated cord blood that does not contain a blood coagulant, for example. The uncoagulated cord blood that does not contain a blood coagulant generally is cord blood introduced directly from a patient. According to the cord blood component preparation device of the present embodiment, it is possible to obtain serum in which platelets are activated with a blood coagulation-accelerating substance that accelerates blood coagulation, in addition to the above-described cord blood stem cells, treated serum, and untreated serum.

Figure 6:
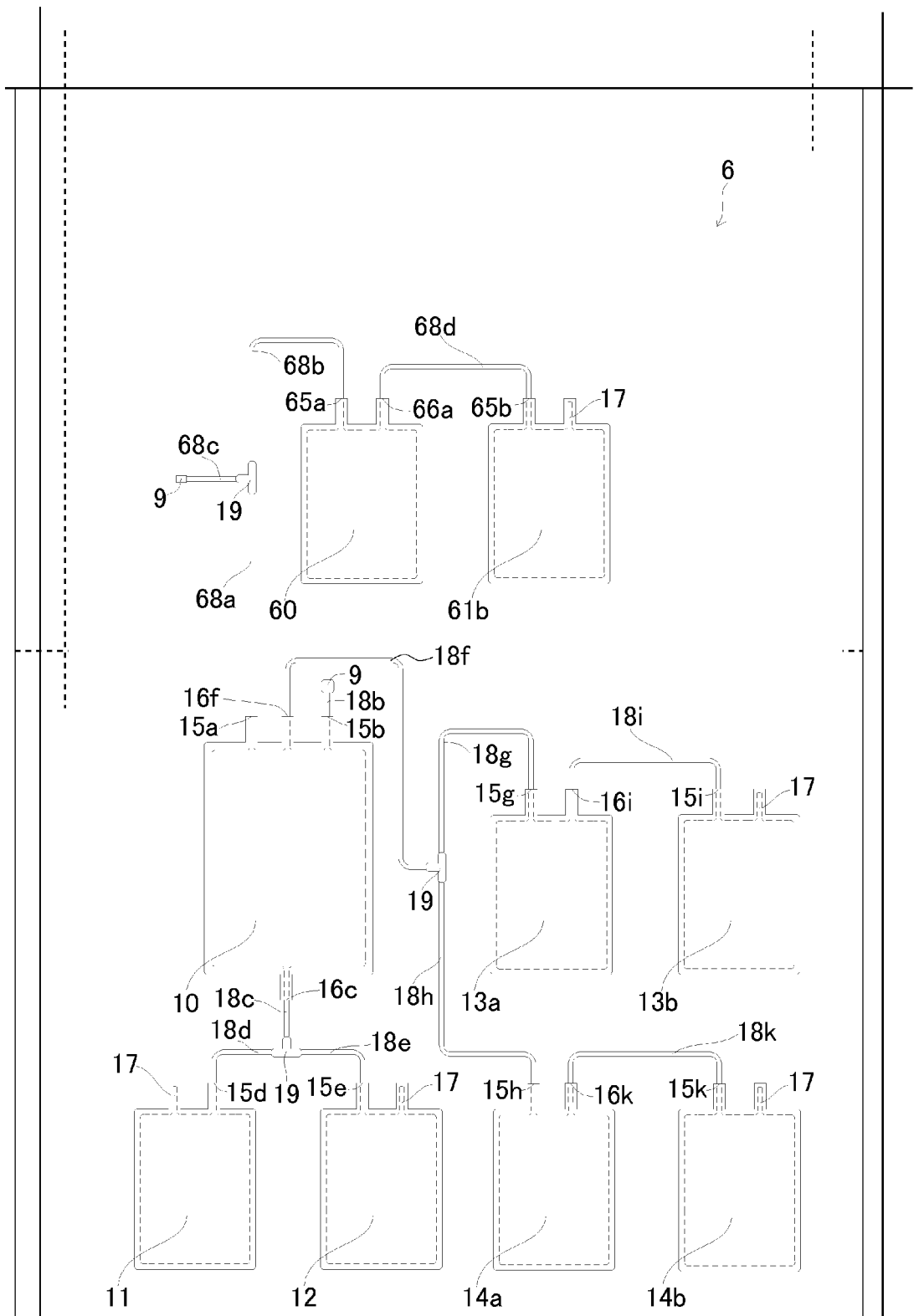
FIG. 6 is a plan view schematically showing an example of still another cord blood component preparation device according to the present invention.

An example of the fourth cord blood component preparation device according to the present invention will be described with reference to FIG. 6. In FIG. 6, elements the same as those in FIGS. 1 to 5 are marked with the same reference numerals. The fourth cord blood component preparation device is the same as the first to third cord blood component preparation devices, unless otherwise stated. Unless otherwise stated, the present invention is not limited thereto.

FIG. 6 is a plan view schematically showing the cord blood component preparation device of the present embodiment. The cord blood component preparation device 6 is the cord blood component preparation device of FIG. 1 illustrating the first embodiment, further including a second storage unit 60 for storing cord blood and a third serum accommodation unit 61b. The storage unit 10 in FIG. 1 corresponds to a first storage unit in the present embodiment. The first storage unit 10 is the same as the storage unit in the first embodiment unless otherwise stated. Also, the respective accommodation units connected to the first storage unit 10 through tubes and the like are the same as those in the first embodiment illustrated in FIG. 1 unless otherwise stated. To the first storage unit 10, a blood coagulation reagent and an erythrocyte sedimenting agent can be introduced. The first storage unit 10 has an inlet 15a for cord blood, and one end of a tube 68a is connected to the inlet 15a. The second storage unit 60 can accommodate a blood coagulation-accelerating substance (blood coagulation accelerator) that accelerates blood coagulation. The second storage unit 60 has an inlet 65a and an outlet 66a. The left inlet 65a of the second storage unit 60 is an inlet for cord blood, and one end of a tube 68b is connected thereto. The tube 68a connected to the first storage unit 10 and the tube 68b connected to the second storage unit 60 are connected to a tube 68c via a branch connector 19. The other end of the tube 68c is a connection part 9 to which a puncture needle or the like for collecting cord blood can be connected. The right outlet 66a of the second storage unit 60 is an outlet for discharging serum after blood coagulation and a tube 68d is connected thereto. Furthermore, the third serum accommodation unit 61b has an inlet 65b, and the other end of the tube 68d connected to the second storage unit 60 is connected to the inlet 65b.

In the cord blood component preparation device of the present embodiment, as will be described below, a blood coagulation cascade is caused to act by the contact of the blood coagulation-accelerating substance with cord blood in the second storage unit, thereby causing the coagulation of blood as well as the release of growth factors by the activation of platelets. Thus, in the second storage unit 60, a supernatant obtained after the blood coagulation contains more growth factors as compared with the case where platelets are not activated.

The blood coagulation-accelerating substance is not particularly limited, and those described in Japanese Patent No. 3788479 and the like can be used, for example. The shape of the blood coagulation-accelerating substance preferably is granular, fine-granular, or massive, for example, and a substantially spherical shape also is preferable. The size of the blood coagulation-accelerating substance is not particularly limited, and it is preferable that the diameter thereof is 1 to 10 mm, more preferably 3 to 5 mm, for example. The blood coagulation-accelerating substance may have a porous structure, for example. When the blood coagulation-accelerating substance has a porous structure, the area per unit volume thereof can be made large, thus allowing the activation of platelets and the like to be carried out efficiently.

The material of the blood coagulation-accelerating substance is not particularly limited. Preferably, the surface of the blood coagulation-accelerating substance is formed of a layer containing a silicon dioxide, for example. Examples of the silicon dioxide include glass, silica, diatomaceous earth, and kaoline. Furthermore, the blood coagulation-accelerating substance may be such that, for example, the core thereof contains a magnetic substance, for example. When the blood coagulation-accelerating substance contains a magnetic substance as described above, it is possible to stir cord blood by, for example, applying a magnetic field to the second storage unit in which the blood coagulation-accelerating substance is accommodated, whereby rapid activation of platelets and the like becomes possible.

The amount of the blood coagulation-accelerating substance in the second storage unit is not particularly limited, and can be determined as appropriate depending on the amount of cord blood that the storage unit can accommodate, for example. As a specific example, it is preferable to set the total surface area of the blood coagulation-accelerating substance to 0.1 to 25 mm$^2$/ml with respect to the volume of cord blood, for example.

A method for preparing cord blood components using the cord blood component preparation device 6 of the present embodiment will be described with reference to an illustrative example. Specific treatment conditions can be set to be the same as those described above, unless otherwise stated.

First, a puncture needle is attached to the connection part 9 of the tube 68c. The tip of the puncture needle is inserted to an umbilical cord, and cord blood is introduced to the tube 68c. Then, the cord blood is introduced to the first storage unit 10 and the second storage unit 60 through the tubes 68a and 68b. The order of introducing the cord blood is not particularly limited, and it may be introduced to these storage units at the same time or sequentially. In the latter case, the introduction of the cord blood can be carried out as follows, for example. First, the cord blood is introduced to the second storage unit 60 with the flow path of the tube 68a connected to the first storage unit 10 being blocked in the vicinity of the branch connector 19. Thereafter, the flow path of the tube 68b connected to the second storage unit 60 is blocked in the vicinity of the branch connector 19 and then the blocking of the tube 68a is released to allow the cord blood to be introduced to the first storage unit 10. After the cord blood is introduced to both the first storage unit 10 and the second storage unit 60, the tubes 68a and 68b between these storage units may be cut off and fused.

In the first storage unit 10, an anticoagulant may be accommodated in advance, or it may be introduced to the first storage unit 10 prior to the introduction of cord blood, as described above, for example. After cord blood is introduced to the first storage unit 10 provided with the anticoagulant, it is possible to obtain the above-described hematopoietic stem cells, treated serum, and untreated serum by conducting the same treatments as in the first embodiment, for example. The respective accommodation units connected to the first storage unit 10 may be the same as those in the second or third embodiment, instead of those in the first embodiment, for example.

On the other hand, in the second storage unit 60, the blood coagulation-accelerating substance may be accommodated in advance, or it may be introduced to the second storage unit 60 prior to the introduction of cord blood, as described above, for example. When the cord blood is introduced to the second storage unit 60 provided with the blood coagulation-accelerating substance, blood coagulation (fibrin formation) occurs in the cord blood, and also, platelets in the cord blood are activated. By this activation, more growth factors are released as compared with the case where the platelets are not activated. Then, after the blood coagulation has occurred, the second storage unit 60 is centrifuged, thus achieving the separation into a sediment fraction containing fibrin, platelets, and the like and a supernatant fraction. This supernatant fraction is introduced to the third serum accommodation unit 61b through the tube 68d connecting the second storage unit 60 and the third serum accommodation unit 61b. Thus, serum containing more growth factors can be collected. Furthermore, according to the present embodiment, since the second storage unit 60 does not contain an anticoagulant, serum free of a neutralizer such as calcium chloride can be obtained, for example.

Next, examples of the present invention will be described. It is to be noted, however, the present invention is by no means limited by the following examples.

EXAMPLES

Example 1

Serum was prepared from cord blood, and the effect of the serum on the proliferation and differentiation of cord blood hematopoietic stem cells was examined.

(1) Preparation of Hematopoietic Stem Cells and Serum 80 ml of cord blood containing a CPD solution as an anticoagulant was introduced to a centrifuge tube, and HES (Hydroxy Ethyl Starch) was added thereto as an erythrocyte sedimenting agent, so that its concentration became 12 mg/ml. The mixture was allowed to stand still at room temperature for 60 minutes, and only a supernatant fraction was collected. This was centrifuged (3920 m/s$^2$ (400×g), 5 minutes), and a supernatant fraction and a sediment fraction were obtained. The supernatant fraction is a platelet-rich plasma fraction, and the sediment fraction is a nucleated cell fraction.

30 ml of the platelet-rich plasma fraction was introduced to a centrifuge tube with a capacity of 50 ml. This was centrifuged (22834 m/s$^2$ (2330×g), 4° C., 10 minutes), and a supernatant fraction was obtained. The supernatant fraction was heated at 56° C. for 30 minutes, and then centrifuged (22834 m/s$^2$ (2330×g), 4° C., 10 minutes) so as to remove fibrin therefrom. Thus, non-sonicated serum was prepared. Hereinafter, this is referred to as cord blood serum (−). On the other hand, 30 ml of the platelet-rich plasma fraction was introduced to a PVC bag of 5 cm×10 cm and subjected to sonication. Thereafter, a heat treatment and centrifuging were performed under the same conditions as in the above. Thus, sonicated serum was prepared. Hereinafter, this is referred to as cord blood serum (+). The sonication was carried out for 30 minutes using an ordinary ultrasonic generator under the conditions where, when ultrasonic waves against an object to be treated were measured with a sound pressure meter, a sound pressure of at least 5 mV could be obtained, with the frequency being set to 45 kHz and the distance from the ultrasonic generator being set to 15 cm.

The following treatment was performed with respect to the nucleated cell fraction to purify hematopoietic stem cells. First, to 0.3 ml of the nucleated cell fraction, 50 µl of magnetic beads (Miltenyi Biotec) having a CD34 antibody immobilized thereon were added, and the resultant mixture was allowed to stand still at 4° C. for 30 minutes. Then, this was applied to a magnetic column (trade name "MS column", Miltenyi Biotec), and hematopoietic stem cells were collected from the nucleated cell fraction. The purity of the collected hematopoietic stem cells was found to be about 70% through the examination by flow cytometry using a fluorescent dye-labeled CD34 antibody (Beckman Coulter, Inc.).

The cord blood serum (+) and the cord blood serum (−) were prepared from cord blood of each of three subjects (A, B, C), and the cord blood hematopoietic stem cells were prepared from one (A) of the three subjects.

(2) Culture of Hematopoietic Stem Cells

A medium having the following composition was prepared using the cord blood serum (−) or the cord blood serum (+) of each of the subjects A, B, and C as serum. Then, the hematopoietic stem cells collected from the subject B were inoculated into each serum-added medium at a density of 1×10$^4$ cells/well and were cultured in the medium at 37° C. for 7 days.

TABLE 1

(Composition of Medium)

| Components | Concentration |
|---|---|
| Iscove's modified Dulbecco's medium (IMDM, Gibco) | 90 v/v % |
| Stem Cell Factor (PeproTech) | 50 ng/ml |
| Flt-3 ligand (PeproTech) | 20 ng/ml |
| Thrombopoietin (R&D Systems) | 10 ng/ml |
| Serum | 10 v/v % |

(3) Measurement of the Number of Cells

After the culture, the collected cells were analyzed by flow cytometry using the above-described labeled CD34 antibody, and the total number of cells per well, the number of hematopoietic stem cells per well, and the proportion of the hematopoietic stem cells to all the cells were calculated.

Comparative Example 1

Culture of hematopoietic stem cells and calculation of the numbers of the respective cells were carried out in the same manner as in Example 1, except that, in the culture of the hematopoietic stem cells, fetal bovine serum (FBS) was used as serum.

Comparative Example 2

Culture of hematopoietic stem cells and calculation of the numbers of the respective cells were carried out in the same manner as in Example 1, except that, in the culture of the hematopoietic stem cells, peripheral blood serum was used as serum. The peripheral blood serum was prepared in the following manner. First, 20 ml of peripheral blood of an adult male was introduced to a centrifuge tube containing two glass beads (bead diameter: 4 mm, Bright Hyoshiki Kogyo K.K.). The centrifuge tube was shaken at room temperature for 20 minutes, then centrifuged ($22050$ m/s$^2$, 4° C., 1.0 minutes), and the supernatant was collected. The supernatant is a plasma fraction. This supernatant was heat-treated at 56° C. for 30 minutes, and filtered through a filter with a pore size of 0.22 µm (PVDF membrane, Millipore Corporation). Thus, peripheral blood serum was prepared.

Figure 7:
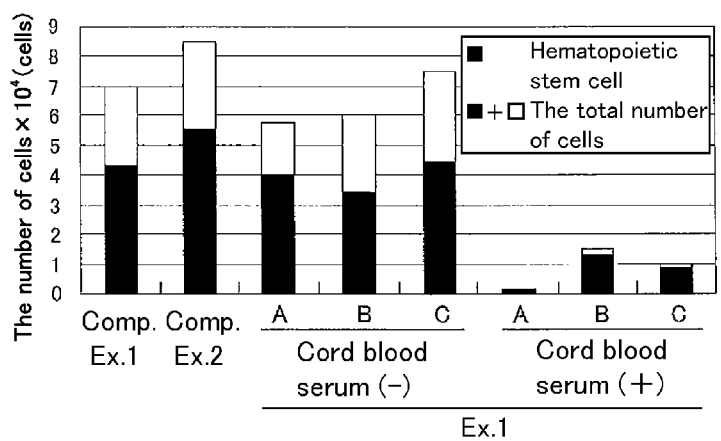
FIG. 7 is a graph showing the number of hematopoietic stem cells cultured in the presence of serum in Example 1.

The graph of FIG. 7 shows the measurement results as to the total number of cells and the number of hematopoietic stem cells per well obtained in Example 1 and Comparative Examples 1 and 2. In the graph of FIG. 7, the vertical axis indicates the number of cells ($\times 10^4$) per well after the culture, and the respective bars indicate, from the left: the result obtained in Comparative Example 1 in which FBS was used; the result obtained in Comparative Example 2 in which the peripheral blood serum was used; the results obtained in Example 1 when the cord blood serums (−) of the subjects A to C were used and the results obtained in Example 1 when the cord blood serums (+) of the subjects A to C were used. The entire bar indicates the total number of cells, and the black portion of the bar indicates the number of hematopoietic stem cells.

As shown in FIG. 7, when the cord blood serums (−) were used in Example 1, the proliferation of the hematopoietic stein cells was observed as in Comparative Example 1 in which FBS was used and Comparative Example 2 in which the peripheral blood serum was used. From this result, it can be said that the cord blood serum (−) can accelerate the proliferation of cord blood hematopoietic stem cells. In contrast, when the cord blood serum (+) was used in Example 1, the total number of the cells was much smaller than those in Comparative Examples 1 and 2. Specifically, when the cord blood serum (+) was used in Example 1, the total number of the cells was $0.165 \times 10^4$ to $1.0 \times 10^4$ and inhibited to 2.4% to 21.4% of the total number of the cells, $7 \times 10^4$, in Comparative Example 1, and to 1.9% to 17.6% of the total number of the cells, $8.5 \times 10^4$, in Comparative Example 2. From this result, it can be said that the cord blood serum (+) can inhibit the proliferation of cord blood hematopoietic stem cells. Further, when the cord blood serum (+) was used in Example 1, the proportion of the hematopoietic stem cells to the total number of the cells was 85% to 88%, which indicates that the proportion of undifferentiated cells to the total number of the cells was high. From this result, it can be said that the cord blood serum (+) also can inhibit the differentiation of hematopoietic stem cells. These results demonstrate that, since the cord blood serum (+) can inhibit the proliferation and differentiation and the cord blood serum (−) can accelerate the proliferation, it is possible to control the proliferation of hematopoietic stem cells as desired by combining them appropriately. In particular, since hematopoietic stem cells to be proliferated and cord blood serums (+) and (−) that can serve as controlling agents can be prepared from the same cord blood, the present invention provides excellent compatibility and safety and also allows effective utilization of cord blood, which used to be discarded. When the cord blood serum (+) was used in the culture of mesenchymal stem cells, it was found that the proliferation was accelerated, contrary to the above result. From this result, it is interpreted that cord blood serum (+) can inhibit the proliferation and differentiation of cord blood stem cells specifically.

Example 21

Hematopoietic stem cells, cord blood serum (+), and cord blood serum (−) were prepared from cord blood of a single subject in the same manner as in Example 1. Then, into the following media to which the respective serums were added, the hematopoietic stem cells were inoculated at a density of $5 \times 10^3$ cells/well, and cultured therein at 37° C. for 14 days. The concentration of the cord blood serum (+) in the medium was set to 5 and 10 v/v %, and the concentration of the cord blood serum (−) in the medium was set to 0.125, 0.25, 0.5, 1, and 2.5 v/v %. Furthermore, as a control, the hematopoietic stem cells were cultured in the same manner using a medium containing neither of the serums. Then, the cells collected after the culture were analyzed by flow cytometry and the number of the hematopoietic stem cells per well were calculated in the same manner as in Example 1.

TABLE 2

| Components | Concentration |
|---|---|
| X-VIVO 10 (Takara Bio Inc.) | Predetermined Concentration (v/v %)* |
| Stem Cell Factor (PeproTech) | 50 ng/ml |
| Flt-3 ligand (PeproTech) | 20 ng/ml |
| Thrombopoietin (R&D Systems) | 10 ng/ml |
| IL-6 (PeproTech) | 50 ng/ml |
| sIL-6α (PeproTech) | 50 ng/ml |
| Serum | Predetermined Concentration (v/v %) |

*100 − serum concentration (v/v %)

The increase rate of the hematopoietic stem cells when the media containing the cord blood serum (+) or the cord blood serum (−) was used is shown in the table below. The increase rate was determined as a relative value, assuming that the number of the hematopoietic stem cells obtained after the culture of 14 days in the serum-free medium was "100%".

TABLE 3

|  | Concentration (v/v %) | Increase rate (%) |
|---|---|---|
| No serum | 0 | 100 |
| Cord blood serum (+) | 5 | 12 |
|  | 10 | 5 |
| Cord blood serum (−) | 0.125 | 128 |
|  | 0.25 | 156 |
|  | 0.5 | 156 |
|  | 1 | 121 |
|  | 2.5 | 124 |

As shown in Table 3, the increase rate of the stem cells could be inhibited by culturing them in the medium containing the sonicated cord blood serum (+) in the range from 5 to 10 v/v %. On the other hand, the increase rate of the stem cells could be increased by culturing them in the medium containing the non-sonicated cord blood serum (−) in the range from 0.125 to 2.5 v/v %.

Example 3

Hematopoietic stem cells, cord blood serum (+), and cord blood serum (−) were prepared from cord blood of a single subject in the same manner as in Example 1. Then, into a medium containing the cord blood serum (−) at a concentration of 0.5 v/v % as in Example 2, the hematopoietic stem cells were inoculated at a density of $5 \times 10^3$ cells/well, and cultured therein at 37° C. for 14 days. The medium containing the cord blood serum (−) at a concentration of 0.5 v/v % was replaced with a medium containing the cord blood serum (+) at a concentration of 10 v/v % as in Example 2 at the 14th day from the start of the culture, and the stem cells were cultured further. Then, the cells collected after the culture for predetermined culture periods (0, 7, 14, and 21 days) were analyzed by flow cytometry and the number of hematopoietic stem cells per well were calculated in the same manner as in Example 1. As a control, the culture was performed using only the serum used initially from the start of the culture under the same serum concentration condition without performing the replacement with the medium containing the cord blood serum (+) at a concentration of 10 v/v % at the 14th day of the culture, and the number of hematopoietic stem cells were calculated.

The increase rate of the hematopoietic stem cells is shown in the following table. The increase rate was determined as a relative value (-fold), assuming that the number of hematopoietic stem cells at the start of the culture (Day 0) was "1".

TABLE 4

|  | With medium replacement Increase rate | Without medium replacement Increase rate |
|---|---|---|
| Day 0 | 1-fold | 1-fold |
| Day 7 | 3.7-fold | 3.9-fold |
| Day 14 | 12.7-fold | 11.0-fold |
| Day 21 | 10.1-fold | 30.2-fold |

As can be seen from Table 4, by culturing the hematopoietic stem cells in the medium containing the cord blood serum (−) at a concentration of 0.5 v/v % and then replacing the medium with the medium containing the cord blood serum (+) at a concentration of 10 v/v % on the 14th day of the culture, the increase in the hematopoietic stem cells was inhibited.

INDUSTRIAL APPLICABILITY

As specifically described above, according to the present invention, it is possible to control the proliferation and differentiation of cord blood hematopoietic stem cells using serum derived from cord blood without using a virus vector having a problem in safety as described above, for example. Specifically, the above-described control is possible using only cord blood serum. Therefore, the present invention is very excellent in safety and can regulate the proliferation and differentiation with simple operations. In particular, since the present invention uses serum derived from cord blood, it is possible to use hematopoietic stem cells and serum derived from cord blood of the same individual, for example. Therefore, cord blood can be used more effectively, and since the components derived from the same individual can be used in combination, the reliability regarding the safety also can be improved. As described above, since the present invention can inhibit the proliferation and differentiation of hematopoietic stem cells, it is particularly useful when delivering the hematopoietic stem cells to a destination, storing the hematopoietic stem cells until a desired time at which the proliferation of the hematopoietic stem cells is started, and the like, for example. Thus, it can be said that the method according to the present invention can further promote the effective utilization of cord blood hematopoietic stem cells in the field of regenerative medicine.

The invention claimed is:

1. A proliferation-controlling agent, comprising:
   a proliferation inhibitor for inhibiting proliferation and differentiation of hematopoietic stem cells, the proliferation inhibitor containing a sonicated liquid component of cord blood.

2. The proliferation-controlling agent according to claim 1, further comprising:
   a proliferation accelerator for accelerating proliferation of hematopoietic stem cells, the proliferation accelerator containing a non-sonicated liquid component of cord blood,
   wherein the proliferation inhibitor and the proliferation accelerator are stored separately from one another.

3. A proliferation-controlling kit, comprising:
   a proliferation inhibitor for inhibiting proliferation and differentiation of hematopoietic stem cells, the proliferation inhibitor containing a sonicated liquid component of cord blood.

4. The proliferation-controlling kit according to claim 3, further comprising:
   a proliferation accelerator for accelerating proliferation of hematopoietic stem cells, the proliferation accelerator containing a non-sonicated liquid component of cord blood,
   wherein the proliferation inhibitor and the proliferation accelerator are stored separately from one another.

5. The proliferation-controlling kit according to claim 4, wherein the liquid component contained in the proliferation inhibitor and the liquid component contained in the proliferation accelerator are derived from cord blood of the same individual.

6. The proliferation-controlling kit according to claim 3, for controlling proliferation of hematopoietic stem cells derived from cord blood of the same individual as the liquid component.

7. The proliferation-controlling kit according to claim 5, wherein the individual is a mammal.

8. The proliferation-controlling kit according to claim 7, wherein the mammal is a human.

9. The proliferation-controlling kit according to claim 4, wherein the proliferation inhibitor is contained in a first container and the proliferation accelerator is contained in a second container.

* * * * *